United States Patent [19]

Ponsford et al.

[11] 4,255,441

[45] Mar. 10, 1981

[54] β-LACTAM ANTIBIOTICS, A PROCESS FOR THEIR PREPAERATION AND THEIR USE IN PHARMACEUTICAL COMPOSITIONS

[75] Inventors: Roger J. Ponsford, Wimblehurst Park; Andrew J. G. Baxter, Albina Garth; Robert Southgate, Warnham, all of England

[73] Assignee: Beecham Group Limited, England

[21] Appl. No.: 4,896

[22] Filed: Jan. 19, 1979

[30] Foreign Application Priority Data

Mar. 14, 1978 [GB] United Kingdom ............... 9985/78

[51] Int. Cl.³ .................. C07D 487/04; A61K 31/40
[52] U.S. Cl. ............................. 424/274; 260/239 A; 260/245.2 T; 542/416
[58] Field of Search ............... 260/326.31, 245.2 T; 424/274; 542/416

[56] References Cited

U.S. PATENT DOCUMENTS

| | | | |
|---|---|---|---|
| 4,153,714 | 5/1979 | Ponsford | 260/326.31 |
| 4,203,902 | 5/1980 | Shih | 260/245.2 T |

Primary Examiner—Mary C. Lee

Attorney, Agent, or Firm—Jacobs & Jacobs

[57] ABSTRACT

The present invention provides the antibacterial agents of the formula (II):

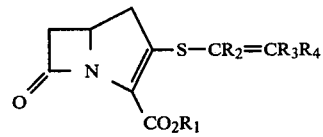

wherein $R_1$ is a group such that $CO_2R_1$ is a carboxylic acid group or a salt thereof or is a group of the formula $CO_2R_1^1$ wherein $R_1^1$ is a group such that $CO_2R_1^1$ is an ester group, $R_2$ is a hydrogen atom or a lower alkyl group; $R_3$ is a hydrogen atom or a lower alkyl group; and $R_4$ is a NH.$CO_nR_6$ group where $R_6$ is a lower alkyl group, a phenyl group or a phenyl group substituted by one or two halogen atoms, lower alkyl or lower alkoxyl groups; and n is 1 or 2.

A process for their preparation and their use in pharmaceutical compositions is also described.

46 Claims, No Drawings

β-LACTAM ANTIBIOTICS, A PROCESS FOR THEIR PREPAERATION AND THEIR USE IN PHARMACEUTICAL COMPOSITIONS

British Pat. No. 1,483,142 discloses that the compound of the formula (I):

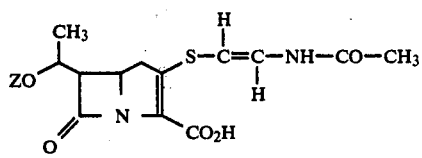

wherein Z is $HO_3S$ and its salts may be obtained by fermentation of strains of *Streptomyces olivaceus*. Danish Patent Application No. 984/78 discloses that the compound of the formula (I) wherein Z is H and its salts could also be obtained by fermentation of strains of that organism. We have found that a distinct class of synthetic antibacterial agents which contain a β-lactam ring fused to a pyrroline ring may be prepared.

Accordingly the present invention provides the compounds of the formula (II):

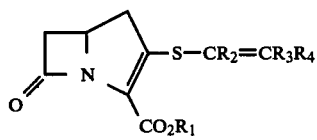

wherein $R_1$ is a group such that $CO_2R_1$ is a carboxylic acid group or a salt thereof or is a group of the formula $CO_2R_1^1$ wherein $R_1^1$ is a group such that $CO_2R_1^1$ is an ester group, $R_2$ is a hydrogen atom or a lower alkyl group; $R_3$ is a hydrogen atom or a lower alkyl group; and $R_4$ is a phenyl group or a phenyl group substituted by one or two groups selected from a fluorine, chlorine, $OR_5$, $NH.CO.R_5$, $NH.CO_2R_5$ or $CO_2R_5$ where $R_5$ is a lower alkyl or benzyl group or $R_4$ is a hydrogen atom or lower alkyl group or $R_4$ is a $CO_2R_5$ group where $R_5$ is a lower alkyl group or benzyl group or $R_4$ is a $NH.CO_nR_6$ group where $R_6$ is a lower alkyl group, a phenyl group or a phenyl group substituted by one or two halogen atoms, lower alkyl or lower alkoxyl groups; and n is 1 or 2.

When used herein the term "lower" means the group contains up to 4 carbon atoms.

Aptly $CO_2R_1$ in the compounds of the formula (II) represents a carboxylic acid group or a salt thereof.

Aptly $CO_2R_1$ in the compounds of the formula (II) represents an ester group $CO_2R_1^1$.

Particularly suitable lower alkyl groups include the methyl and ethyl groups. A preferred lower alkyl group is the methyl group.

A favoured value for $R_2$ is a hydrogen atom.

Favoured values for $R_3$ include the hydrogen atom and the methyl group.

A preferred value for $R_3$ is the hydrogen atom.

Suitably $R_4$ is a phenyl group or a phenyl group substituted by one or two groups selected from fluorine, chlorine, $OR_5$, $NH.CO.R_5$, $NH.CO_2R_5$ or $CO_2R_5$ where $R_5$ is a lower alkyl or benzyl group or $R_4$ is a hydrogen atom or lower alkyl group or $R_4$ is a $CO_2R_5$ group where $R_5$ is a lower alkyl or benzyl group.

Suitably $R_4$ is a $NH.CO_nR_6$ group where $R_6$ is a lower alkyl group, a phenyl group or a phenyl group substituted by one or two halogen atoms, lower alkyl or lower alkoxyl groups; and n is 1 or 2.

From the foregoing it will be realised that certain favoured compounds of this invention include those of the formula (III) and (IV):

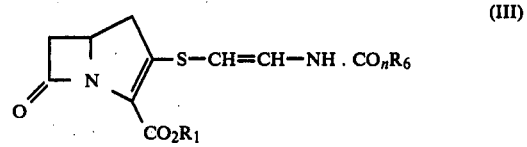

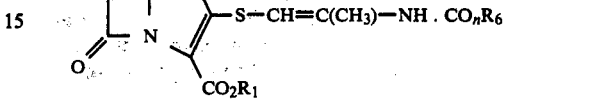

wherein $R_1$, n and $R_6$ are as defined in relation to formula (II).

Most suitably n is 1.

Similarly it will be realised that other favoured compounds of this invention include those of the formula (V):

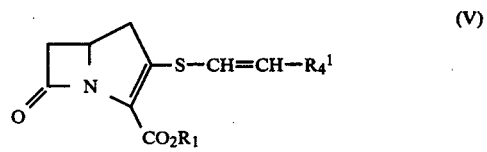

where $R_1$ is as defined in relation to formula (II) and $R_4^1$ is a group $R_4$ as defined in relation to formula (II) excluding the $NH.CO_nR_6$ group.

Suitably $R_4^1$ is a phenyl group optionally monosubstituted.

Suitable groups $R_4$ include the phenyl, p-chlorophenyl, m-chlorophenyl, p-nitrophenyl, m-nitrophenyl, p-ethoxycarbonylphenyl, p-fluorophenyl, p-methylphenyl, p-methoxyphenyl and like groups.

Other suitable groups $R_4$ include the hydrogen atom and the methyl and ethyl groups.

Yet other suitable groups $R_4$ include those of the formula $CO_2R_7$ where $R_7$ is methyl, ethyl, phenyl or benzyl.

It will be realised that the compounds of the formula (II) may be in either of two geometrical forms about the exocyclic double bond as shown in the sub-formulae (a) and (b) thus:

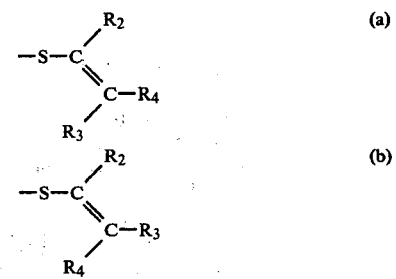

Both separated geometrical isomers and mixtures of said isomers are within the scope of this invention.

In the compounds of the formulae (II)-(V) $CO_2R_1$ is favourably a carboxylic acid group or a salt thereof.

Most favourably $CO_2R_1$ represents a salted carboxylic acid group wherein the cation is pharmaceutically acceptable. Preferred pharmaceutically acceptable salts include the sodium, potassium, calcium and magnesium salts of which the sodium salt is particularly preferred.

Suitable groups $R_1^1$ include alkyl groups of up to 12 carbon atoms, alkenyl groups of up to 12 carbon atoms, alkynyl groups of up to 12 carbon atoms, phenyl or benzyl groups or any aforesaid inertly substituted by lower alkoxyl, lower acyloxyl, halogen, nitro or the like group. Used herein 'inertly substituted' means that the resulting group is stable and will not undergo rapid decomposition.

Particularly suitable groups $R_1^1$ include lower alkyl groups optionally substituted by lower alkoxyl group; the benzyl group optionally substituted by lower alkoxyl, nitro, chloro or the like; and those groups which are known to give rise to rapid in-vivo hydrolysis in penicillin esters.

Certain preferred groups $R_1^1$ include the methyl, ethyl, methoxymethyl, 2-methoxyethyl, benzyl, methoxybenzyl and the like. Other preferred groups $R_1^1$ include those which give rise to in-vivo hydrolysable esters such as the acetoxymethyl, pivaloyloxymethyl, α-ethoxycarbonyloxyethyl, phthalidyl and the like.

An especially preferred group $R_1^1$ is the phthalidyl group.

A further especially preferred group $R_1^1$ is the p-nitrobenzyl group.

The compounds of the formula (II) most suitably have the configuration shown in formula (VI):

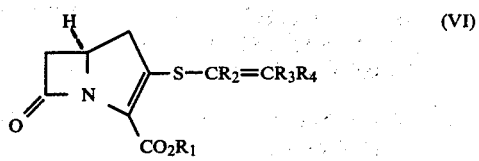

wherein $R_1$, $R_2$, $R_3$ and $R_4$ are as defined in relation to formula (II).

Thus the compounds of the invention are preferably those having the S- configuration at C-5. However, mixtures of the compounds of the formula (VI) with their enantiomers, for example the 5RS compounds, are also included within this invention.

A reaction sequence leading to the compounds of this invention is as follows:

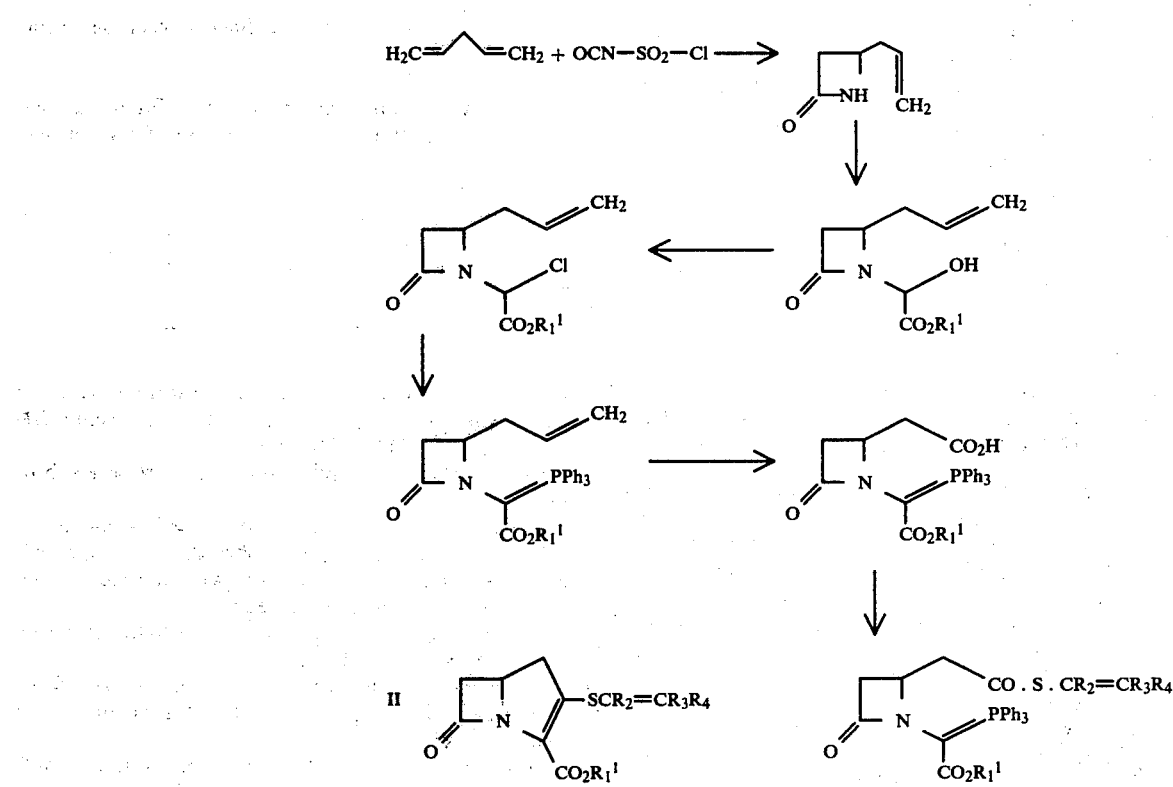

The process provided by this invention for the preparation of the compounds of the formula (II) comprises the ring closing elimination of the elements of triphenylphosphineoxide from a compound of the formula (VII):

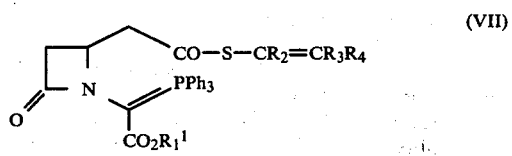

wherein $R_1^1$, $R_2$, $R_3$ and $R_4$ are as defined in relation to formula (II); and thereafter cleaving the ester to yield the carboxylic acid or its salt.

The ring closure is normally brought about by heating the compound of the formula (VII) in an inert solvent; for example temperatures of 90°–120° and more suitably 100°–110° C. may be employed in a solvent such as toluene or the like. The reaction is best carried out under dry conditions under an inert gas.

The ester of the compound (II) produced may be isolated by any standard method such as fractional crystallisation or chromatography. We have found that it is most convenient to separate the desired product by column chromatography.

Any convenient ester may be used in the process of this invention. Since it is frequently desirable to form a salt of compounds (II), the ester employed is preferably one which is readily converted to the parent acid or its salt by mild methods of hydrogenolysis. In a further aspect therefore the invention includes a process for preparing a salt or free acid of a compound (II) which process comprises de-esterifying an ester of a compound of formula (II). Particularly suitable esters for use in this process include benzyl esters, optionally substituted in the para position by a lower alkoxy, or nitro group or a halogen atom.

A preferred ester for use in this process is the p-nitrobenzyl ester.

Esters of compounds (II) may be de-esterified by conventional methods of hydrogenolysis.

Suitable methods include hydrogenation in the presence of a transition metal catalyst. The pressure of hydrogen used in the reaction may be low, medium or high but in general an approximately atmospheric or slightly super-atmospheric pressure of hydrogen is preferred. The transition metal catalyst employed is preferably palladium on charcoal or on calcium carbonate. The hydrogenation may be effected in a suitable solvent in which the ester is soluble such as aqueous dioxan or the like. If this hydrogenation is carried out in the presence of a base then a salt of compounds (II) is produced. Suitable bases for inclusion include $NaHCO_3$, $KHCO_3$, $Na_2CO_3$, $K_2CO_3$, $CaCO_3$, $MgCO_3$, $LiHCO_3$, $NH_4OCOCH_3$ and the like. If no base is present then hydrogenation leads to the preparation of an acid within formula (II) which may then be neutralised if desired to yield a salt. Suitable bases which may be used to neutralise acids within formula (II) include LiOH, NaOH, $NaHCO_3$, KOH, $Ca(OH)_2$ and $Ba(OH)_2$.

The salts of acids (II) may be converted to esters in conventional manner, for example by reaction with a reactive halide such as bromophthalide in solution in dimethylformamide or like solvent.

The compound of the formula (VII) may be prepared by the reaction of a corresponding compound of the formula (VIII):

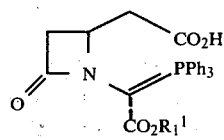

(VIII)

wherein $R_1^1$ is as defined in relation to formula (VII) with a diloweralkylphosphorochloridate and a triloweralkylamine followed by reaction with a thallium, silver, sodium or lithium salt of the compound of the formula (IX):

$$H-S-CR_2=CR_3R_4 \quad (IX)$$

where $R_2$, $R_3$ and $R_4$ are as defined in relation to formula (II).

Aptly a sodium, silver or thalliumsalt of the compound of the formula (IX) is employed.

A particularly suitable diloweralkylphosphorochloridate is diethylphosphorochloridate.

A particularly suitable triloweralkylamine is triethylamine.

The compound of the formula (VIII) may alternatively be converted to the acid chloride or anhydride by conventional means and reacted with the salt of the compound of the formula (IX) to yield the compound of the formula (VII).

The preceeding reactions are generally carried out in an inert organic solvent such as tetrahydrofuran at a non-extreme temperature such as 0° to 40° C., for example 15°–25° C.

The compound of the formula (VIII) may be prepared by the reaction of the compound of the formula (X):

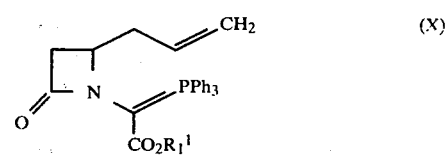

(X)

wherein $R_1^1$ is as defined in relation to formula (VIII) with ozone in the presence of trifluoroacetic acid followed by m-chloroperbenzoic acid.

The ozonolysis is generally performed at a depressed temperature such as −40° to −80° C., for example about −70° C. and in solution in an inert solvent such as methylene chloride. Excess ozone is removed by flushing with an inert gas and thereafter a solution of the peracid is added to the reaction mixture.

The compound of the formula (X) may be prepared from the corresponding compound of the formula (XI):

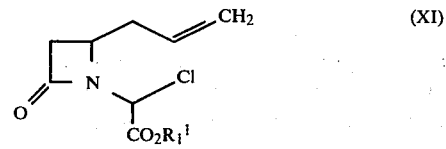

(XI)

wherein $R_1^1$ is as defined in relation to formula (X) by reaction with triphenylphosphine.

This reaction is normally effected in the presence of at least one equivalent of a base of relatively low nucleophilicity such as 2,6-lutidine at an ambient temperature in a dry solvent such as dioxan, tetrahydrofuran or the like.

The compound of the formula (XI) may be prepared from the corresponding carbinol of the formula (XII)

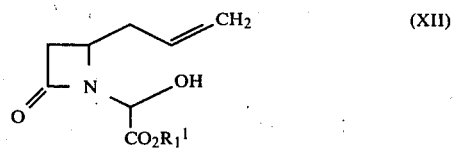

(XII)

by reaction with thionyl chloride.

This reaction is also normally effected in the presence of at least one equivalent of a base of relatively low nucleophilicity in a dry solvent such as dioxane or tetrahydrofuran but in this instance the reaction is performed at a depressed temperature, for example −30° to −10° C.

The preceding carbinol may be prepared by the reaction of a compound of the formula (XIII):

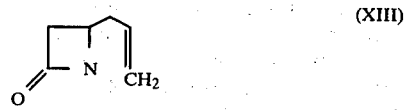

with a glyoxylic acid ester of the formula (XIV):

wherein $R_1^1$ is as defined in relation to formula (II) or alternatively by reaction with glyoxylic acid followed by esterification in conventional manner.

Normally this reaction is carried out in an inert solvent at an elevated temperature, for example in dry benzene under reflux.

The compound of the formula (XIII) may be prepared as described in Description 1 hereinafter.

The present invention also provides a pharmaceutical composition which comprises a compound of the formula (II) as hereinbefore defined and a pharmaceutically acceptable carrier.

Most suitably the composition will be in unit dosage form and will comprise 25–1000 mg and more usually 50–500 mg of a compound of the formula (II). The compositions may be adapted for oral or parenteral administration.

Preferably the compound of the formula (II) present in such compositions will be in-vivo hydrolysable to the parent acid or its salt.

The composition of this invention may beneficially also comprise a penicillin or cephalosporin. Certain particularly suitable penicillins for use in these compositions include amoxycillin trihydrate and sodium amoxycillin.

Sterile salts in water for injection B.P. may be used, for example a sodium salt of an antibacterial agent or agents, for example at a concentration of 50–100 mg per mil of the sodium salt of a compound of the formula II and 100–250 mg per mil of the sodium salt of amoxycillin.

The salts of the compounds of the formula (IX) wherein $R_2$ and $R_3$ are hydrogen and $R_4$ is a $NH.CO_nR_6$ as defined in relation to formula (II) are novel and as such form an aspect of this invention. Preferred compounds of the formula (IX) are these wherein n is 1 and $R_6$ is methyl. Suitable salts of these compounds include the sodium, thallium, silver and lithium salts.

Intermediates useful for the preparation of this invention may be prepared by the general methods set forth in German OLS No. P2811514.2, U.S. Ser. No. 930225 or European Patent Application No. 78300231.4.

The following Examples illustrate this invention. The following Descriptions relate to the preparation of useful intermediates.

DESCRIPTION 1

4-Allyl-1-(1-tert-butyloxycarbonyl-1-triphenylphosphoranylidenemethyl) azetidin-2-one (i) Preparation of 4-allyl azetidin-2-one

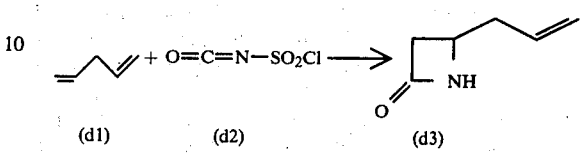

1,4-Pentadiene (d1) (30 g) and chlorosulphonyl isocyanate (d2) (35.4 ml) were mixed and allowed to stand at room temperature for 3 days, in a pressure bottle. The thick, dark syrup obtained was diluted with methylene chloride (500 ml) and added dropwise to a stirred solution of sodium sulphite (66 g) in water (240 ml). The pH was maintained between 6.5 and 7.5 by the addition of 10% aqueous potassium hydroxide (600 ml in total). The lower organic phase was separated and the aqueous phase extracted (×2) with ethyl acetate. The combined organic extracts were dried over magnesium sulphate, filtered, and evaporated to give the crude azetidinone (d3) as a red oil (16.05 g). This was sufficiently pure for use in subsequent reactions e.g. Description 1 (ii), but could be further purified by distillation b.p. 76°–80°/0.2 mm. $\nu_{max}$ (CHCl$_3$) 3490, 1770 (strong), 1650 (weak) cm$^{-1}$. δ ppm (CDCl$_3$) 2.39 (2H, t, J 6 Hz, CH$_2$), 2.61 (1H, ddd, J 14 Hz, 2 Hz, 1.5 Hz, collapsing with D$_2$O to dd, J 14 Hz, 2 Hz, C3-H), 3.10 (1H, ddd, J 14 Hz, 5 Hz, 2 Hz, collapsing with D$_2$O to dd, J 14 Hz, 5 Hz, C3-H), 3.55–3.91 (1H, m, C4-H), 4.98–6.21 (3H, complex pattern, CH=CH$_2$), 6.67 (1H, broad s, exch. D$_2$O) (Found: M, 111.0683. C$_6$H$_9$NO requires M, 111.0684).

(ii) Preparation of 4-allyl-1-(1-hydroxy-1-tert-butyloxycarbonylmethyl) azetidin-2-one

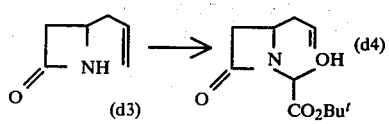

tert-Butyl glyoxylate hydrate (6.22 g) in benzene (120 ml) was refluxed for 1 hour in a Dean-Stark apparatus to remove the water. The azetidinone (d3) (2.31 g) was then added and the reaction mixture refluxed for 4 hours. Chromatography of the crude product as in description 3(i) gave the alcohol (d4) as a pale yellow oil (4.48 g). $\nu_{max}$ (CHCH$_3$) 3490, 1755, 1735, 1640 (weak) cm$^{-1}$ δ ppm (CDCl$_3$) 1.50 (9H, s, Bu$^t$), 2.20–3.25 [4H, 2.66 (1H, dd, J 3 Hz, 14 Hz, C3-H), and 3.09 (1H, dd, J 14 Hz, 5 Hz, C3-H) obscurring 2H, CH$_2$[; 3.68–4.10 (1H, m, C4-H), 4.47 (1H, broad s, exch. D$_2$O, OH); 4.98–5.37 (3H, m, sharpening with D$_2$O), 5.52–6.23 (1H, m. CH=CH$_2$) . M$^+$ at m/e 241 and (m/e +1).

(iii) Preparation of 4-allyl-1-(1-tert-butyloxycarbonyl-1-triphenylphosphoranylidenemethyl)azetidine-2-one

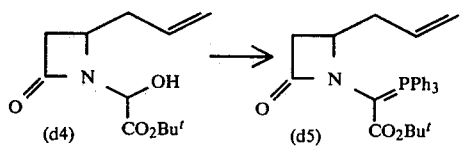

A stirred solution of the alcohol (d4) (4.2 g) in dry tetrahydrofuran (120 ml) under argon, was cooled to −20°, and treated with lutidine (4.03 ml) in tetrahydrofuran (15 ml). Thionyl chloride (2.54 ml) in tetrahydrofuran (15 ml) was added dropwise. After allowing to reach 0° over 30 minutes, the solution was filtered, the lutidine hydrochloride being washed with toluene.

The combined filtrate and washings were evaporated to dryness. The residue was taken up in dry dioxan (100 ml) and treated with lutidine (4.03 ml) and triphenylphosphine (9.1 g). After stirring at room temperature overnight, the phosphorane (d5) was isolated as in description 3 (ii) and obtained as white crystals (4.62 g) from ether m.p. 188°-9°, $\nu_{max}$ (CHCl$_3$) 1730, 1638, 1610 cm$^{-1}$ (Found: C, 74.1; H, 6.8; N, 3.0; P, 6.2% C$_{30}$H$_{32}$NO$_3$P requires C, 74.2; H, 6.6; N, 2.9; P, 6.4%).

DESCRIPTION 2

4-Allyl-1-(1-methoxycarbonyl-1-triphenylphosphoranylidenemethyl)azetidin-2-one

(i) Preparation of 4-allyl-1-(1-hydroxy-1-methoxycarbonylmethyl)azetidin-2-one

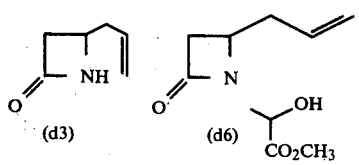

Methyl glyoxylate hydrate (9.75 g) in benzene (500 ml) was refluxed for 1 hour in a Dean-Start apparatus to remove the water. The azetidinone (d3) (2.68 g) was then added and the reaction mixture refluxed for 2 hours. A further portion of the azetidinone (1.34 g) (d3) was then introduced, and refluxing continued for 3 hours. Chromatography of the crude product as in description 3(i) gave the alcohol (d6) as a pale yellow oil (5.33 g). $\nu_{max}$ (CHCl$_3$) 3500, 3350 (broad), 1760–1740 (strong), 1640 (weak) cm$^{-1}$. δ ppm (CDCl$_3$) 2.24–2.90 (3H, m, including [1H, dd, J 3 Hz, 14.5 Hz at δ 2.68]), 3.11 (1H, dd, J 4.5 Hz, 14.5 Hz), 3.72–4.42 (5H, including [3H, s, at δ 3.90], 1H, exch. D$_2$O), 5.00–6.29 (4H, m including [1H, s, at δ 5.48]).

(ii) Preparation of 4-allyl-1-(1-methoxycarbonyl-1-triphenylphosphoranylidenemethyl)azetidin-2-one

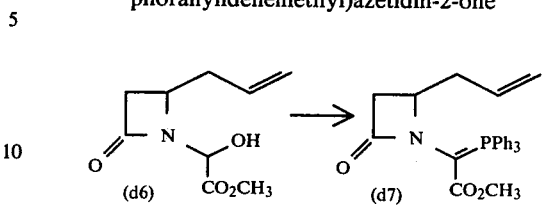

A stirred solution of the alcohol (d6) (5.23 g) in dry tetrahydrofuran (150 ml) under argon, was cooled to −20°, and treated with lutidine (6.06 ml) in tetrahydrofuran (20 ml). Thionyl chloride (3.83 ml) in tetrahydrofuran (20 ml) was added dropwise. After allowing to reach 0° over 20 minutes, the solution was filtered, the lutidine hydrochloride being washed with toluene.

The combined filtrate and washings were evaporated to dryness. The residue was taken up in dry dioxan (13.7 g). After stirring at room temperature, overnight, the phosphorane (d7) was isolated as in Description 3(ii) and obtained as white crystals (7.3 g) from ether m.p. 208°-212°. $\nu_{max}$ (CHCl$_3$) 1738, 1640, 1620 cm$^{-1}$ (Found: C, 72.6; H, 5.9; N, 3.0%. C$_{27}$H$_{26}$NO$_3$P requires C, 73.1; H, 5.9; N, 3.2%).

DESCRIPTION 3

4-Allyl-1-(1-benzyloxycarbonyl-1-triphenylphosphoranylidenemethyl)azetidin-2-one

(i) Preparation of 4-allyl-1-(1-hydroxy-1-benzyloxycarbonylmethyl)azetidin-2-one

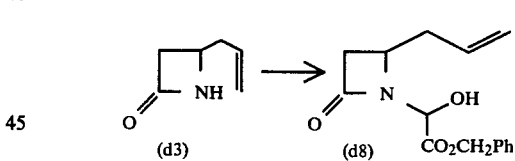

Benzyl glyoxylate hydrate (6 g) in benzene (120 ml) was refluxed for 0.5 hours in a Dean-Stark apparatus to remove the water. The azetidinone (d3) (2.13 g) was added and the reaction mixture refluxed for 4 hours. The solution was cooled, evaporated, and chromatographed on silica gel, eluting with ethyl acetate-petroleum ether mixtures to give a colourless oil (5.6 g) consisting mainly of the isomers of (d8) and sufficiently pure for use in subsequent reactions. Rechromatography of a small portion of this oil, eluting with chloroform gave (d8) as an oil. $\nu_{max}$ (CHCl$_3$) 3420, 1750 (strong), 1640 (weak) cm$^{-1}$. δ ppm (CDCl$_3$) 1.90–3.50 [4H, m, including δ 2.53 (1H, dd, J 15 Hz, 2 Hz, C3-H), 2.92 (1H, dd, J 15 Hz, 5 Hz, C3-H), obscuring 2H, CH$_2$], 4.52 (1H, broad, s, exch. D$_2$O, -OH), 4.85–5.90 [6H, m, including δ 5.40 (1H, broad, collapsing with D$_2$O to singlet, H-C-OH)+complex pattern for CH$_2$Ph and CH=CH$_2$], 7.29 (5H, s).

(ii) Preparation of 4-allyl-1-(1-benzyloxycarbonyl-1-triphenylphosphoranylidenemethyl)azetidin-2-one

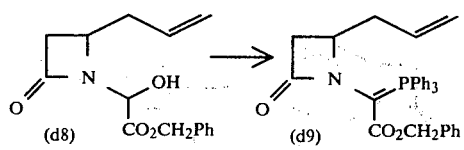

A stirred solution of the alcohol (d8) (6.6 g) in dry tetrahydrofuran (200 ml), under argon, was cooled to −20°, and treated with lutidine (5.13 g) in tetrahydrofuran (10 ml). Thionyl chloride (5.70 g) in tetrahydrofuran (20 ml) was added dropwise. After allowing to reach 0° over 20 minutes the precipitated solid was filtered off, washing with dry toluene.

The combined filtrate and washings were evaporated to dryness and the residue taken up in dry toluene, filtered and evaporated. The gum obtained was taken up in dioxan (200 ml) and treated with triphenylphosphine (12.6 g) and lutidine (5.53 ml). After stirring under argon at room temperature for 3 hours and standing overnight, the precipitated solid was filtered off. The filtrate was evaporated to dryness. Chromatography on silica gel eluting with ethyl acetate-petroleum ether mixtures, gave the required phosphorane, initially as a foam, which crystallised from ether (5.70 g) m.p. 150°–156°. $\nu_{max}$ (CHCl$_3$) 1730, 1638, 1610 cm$^{-1}$.

DESCRIPTION 4

Preparation of 1-(1-t-butoxycarbonyl-1-triphenylphosphoranylidenemethyl)-4-carboxymethylazetidin-2-one

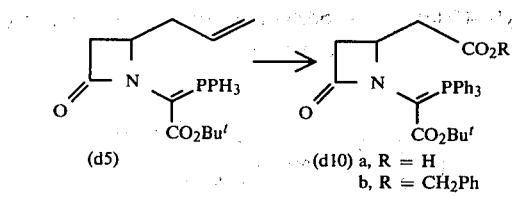

The phosphorane (d5) (prepared as in Description 1) (2 g) was dissolved in dry methylene chloride (100 ml) and treated with trifluoroacetic acid (3.2 ml). The solution was cooled to −70° and ozonised until the solution turned blue. Excess ozone was removed by passing through argon and m-chloroperbenzoic acid (720 mg) in methylene chloride (20 ml) was added. The mixture was allowed to reach RT and stirred overnight. The solvent was evaporated and the residue chromatographed on Merck Kieselgel 60 (<230 mesh). Elution with 50% ethanol/ethyl acetate gave the phosphorane-acid (d10,a) as a colourless foam which crystallised from ethyl acetate/ether (1.6 g) as a mixture of zwitterion and trifluoroacetic acid salt, $\nu_{max}$ 1770, 1750, 1670, 1590 cm$^{-1}$.

The product (1.6 g) was taken up in CHCl$_3$ (50 ml) and stirred with basic alumina (4 g) overnight. The solution was filtered, the solvent evaporated and the residue triturated with ether to yield the phosphorane-acid (d10,a) as a white solid (0.9 g) m.p. 141°–143°. $\nu_{max}$ (CHCl$_3$) 1750, 1595, 1590 cm$^{-1}$.

The acid (d10,a) was further characterised by treatment with benzyl bromide and potassium carbonate in dimethylformamide to give the benzyl ester (d10,b) obtained as white crystals (ex ether) m.p. 176.5°–178°. $\nu_{max}$ (CHCl$_3$) 1735, 1640, 1610 cm$^{-1}$ (Found: C, 72.20; H, 6.59; N, 2.28. C$_{36}$H$_{36}$NO$_5$P requires C, 72.83; H, 6.11; N, 2.36%).

DESCRIPTION 5

Preparation of 1-(1-methoxycarbonyl-1-triphenylphosphoranylidenemethyl)-4-carboxymethylazetidine-2-one

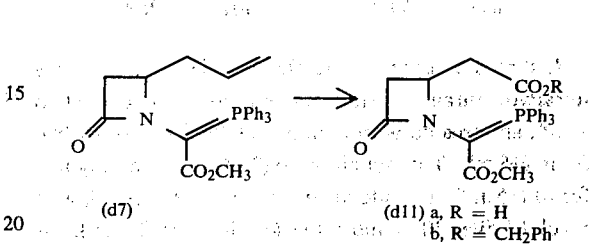

The phosphorane (d7) (Prepared as in Description 2). (4.47 g) in dry methylene chloride (250 ml), was treated with trifluoroacetic acid (7.7 ml). The solution, cooled to −70°, was ozinised until it became blue. After passing argon through to remove excess ozone, m-chloroperbenzoic acid (1.74 g) in methylene chloride (50 ml) was added. The stirred mixture was allowed to reach room temperature, and after stirring overnight, was evaporated to dryness. After re-evaporation from dry toluene the residue was chromatographed on Merck Kieselgel 60. Elution with ethyl acetate gave m-chlorobenzoic acid. Further elution with 10% ethanol in ethyl acetate gave the phosporane-acid (d11 a), partially as the trifluoroacetic acid salt, as a yellow foam (3.7 g), $\nu_{max\,(CH_2Cl_2)}$ 1770, 1755, 1738, 1705–1675 (several weak peaks), 1585 cm$^{-1}$.

This foam was taken up in dry methylene chloride (70 ml), and stirred with basic alumina (8 g), for 2 hours. Evaporation of the filtered solution gave a foam (3 g). Trituration with ether gave the zwitterionic form of the acid-phosphorane (d11 a), as a pale yellow solid, which was collected and dried in vacuo (2.35 g) $\nu_{max}$ (CH$_2$Cl$_2$) 1750, 1740, 1590 cm$^{-1}$.

The acid (d11 a) was characterised by treatment with benzyl bromide and potassium carbonate in dimethylformamide to give the benzyl ester (d11 b), as white crystals (ex ethyl acetate/petroleum ether), m.p. 146°–148°, $\nu_{max}$ (CHCl$_3$) 1740, 1620 cm$^{-1}$ (Found: C, 71.71; H, 5.67; N, 2.44. C$_{33}$H$_{30}$NO$_5$P requires C, 71.87; H, 5.44; N, 2.54%).

DESCRIPTION 6

Preparation of 1-(1-Benzyloxycarbonyl-1-triphenylphosphoranylidenemethyl)-4-carboxymethylazetidin-2-one

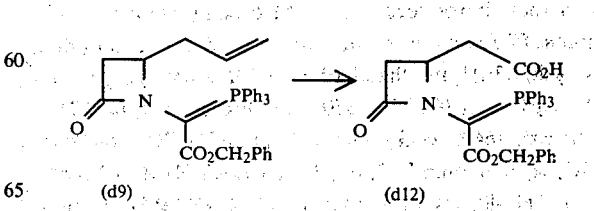

The phosphorane (d9, prepared as in Description 3). (2.076 g) in dry methylene chloride (120 ml) was treated with trifluoroacetic acid (3.08 ml). The solution, cooled to −70°, was ozonized until it became blue. After passing argon through to remove excess ozone, m-chloroperbenzoic (0.69 g) in methylene chloride (25 ml) was added. The stirred mixture was allowed to reach room temperature. After stirring for 3 days work up and chromatography as in description 4 gave the phosphorane acid (d12) partially as the trifluoroacetic acid salt, as a yellow foam (1.215 g), $\nu_{max}$ (CHCl$_3$) 1770 (shoulder) 1750, 1730, 1700, 1665, 1590, 1575 cm$^{-1}$.

This foam was taken up in chloroform (20 ml) and stirred with basic alumina (4 g) for 4 hours. Evaporation of the filtered solution gave the zwitterionic form of the acid-phosphorane (d12) as a foam (0.855 g) $\nu_{max}$ (CHCl$_3$) 1735, 1590, 1585, 1575 cm$^{-1}$.

DESCRIPTION 7

4-Allyl-1-(1-p-nitrobenzyloxycarbonyl-1-triphenyl-phosphoranylidenemethyl)azetidin-2-one (i) Preparation of allyl-1-(1-hydroxy-1-p-nitrobenzyloxycarbonylmethyl-)azetidin-2-one

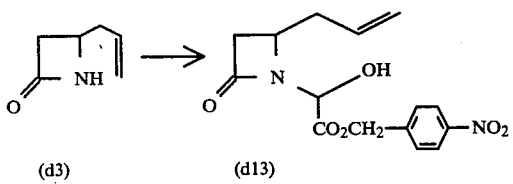

p-Nitrobenzylglyoxylate hydrate (6.8 g) in benzene (120 ml) was refluxed for one hour with removal of water (Dean-Stark). The azetidinone (d3) (3 g) was added and the mixture refluxed for two hours. The solution was cooled, the solvent evaporated and the residue chromatographed. Elution with 80% ethyl acetate/petroleum ether (60°–80°) gave the product (d13). The product was rechromatographed to complete purification and collected as an oil (3.2 g) (37%). $\nu_{max}$ (CHCl$_3$) 3.500 (OH), 1755 (br), 1530, 1355 cm$^{-1}$. δ ppm (CDCl$_3$) 2.39 (2H, m, C$\underline{H}_2$CH=CH$_2$) 2.61 (1H, dd, J 16 Hz, 4 Hz, C3-H) 3.05 (1H, dd, J 16 Hz, 6 Hz, C3-H) 3.92 (1H, m, C4-H) 4.63 (1H, m, collapsing to a singlet on D$_2$O exchange, C$\underline{H}$-OH) 4.80 to 5.80 (6H, complex pattern including C$\underline{H}_2$PhNO$_2$ at 5.35, OH [exchangeable] and C$\underline{H}$=C$\underline{H}_2$) 7.56 and 8.23 (4H, ABq, J 8 Hz, aromatics).

(ii) Preparation of 4-allyl-1-(1-p-nitrobenzyloxycarbonyl-1-triphenylphos-phoranylidenemethyl)azetidin-2-one

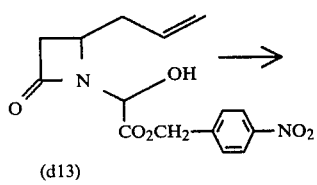

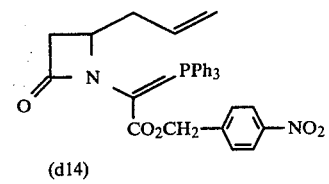

A stirred solution of the alcohol (d13) (1.6 g) in dry THF (100 ml) was treated with 2,6-lutidene (1.07 g) and thionyl chloride (1.19 g) in THF (20 ml) at −20° and stirring continued for 20 minutes. The mixture was filtered the solvent evaporated and the residue azeotroped twice with toluene. It was dissolved in dioxan (100 ml), and 2,6-lutidene (1.07 g) and triphenylphosphine (2.62 g) were added. The reaction was stirred overnight at R.T. and filtered. The solvent was evaporated and the residue chromatographed to yield the product (d14), after decolourising with charcoal (ethanol/ethyl acetate) and trituration of the evaporated solution with ether, as a light yellow solid (1.5 g; 53%) m.p. 182°–183°. $\nu_{max}$ (CHCl$_3$) 1740, 1620, 1525, 1355 cm$^{-1}$. (Found: C, 70.26; H, 5.33; N, 4.80. C$_{33}$H$_{29}$N$_2$O$_5$P requires C, 70.21; H, 5.14; N, 4.96%).

DESCRIPTION 8

Preparation of 1-(1-p-Nitrobenzyloxycarbonyl-1-triphenylphos-phoranylidenemethyl)-4-carboxymethylazetidin-2-one

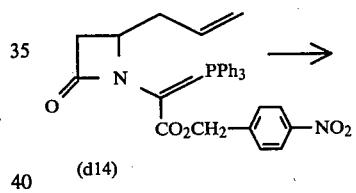

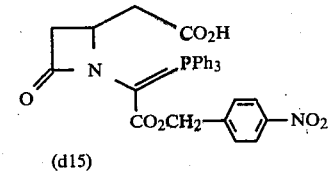

The phosphorane (d14, prepared as in Description 7) (2.82 g) in dry methylene chloride (125 ml) was treated with trifluoroacetic acid (4 ml) at 0°. The solution was cooled to −70° and treated with ozone until blue. Argon was passed through to remove excess ozone and m-chloroperbenzoic acid (0.9 g) in methylene chloride (20 ml) was added and the mixture stirred at R.T. overnight. The solvent was evaporated and the resulting white solid dissolved in ethyl acetate and chromatographed on silica gel. Elution with 10% ethanol/ethyl acetate gave the product as the trifluoroacetic acid salt. The product was stirred in ethyl acetate with basic alumina (6 g) for two hours. Evaporation of the solvent and trituration of the residue with ether gave the acid (d15) as a light yellow hygroscopic solid (2 g; 69%).

A small portion crystallised from ether gave a microcrystalline solid m.p. 127°–133°. $\nu_{max}$ (CHCl$_3$) 1745, 1600, 1355, 1115 cm$^{-1}$. (Found: C, 64.59; H, 4.82; N, 4.66; C$_{32}$H$_{27}$N$_2$O$_7$P. ½H$_2$O requires C, 64.97; H, 4.73; N, 4.73).

EXAMPLE 1

Benzyl 3-Ethenylthio-7-oxo-1-azabicyclo[3.2.0]hept-2-ene-2-carboxylate (a) Preparation of 1-(1-Benzyloxycarbonyl-1-triphenylphosphoranylidenemethyl)-4-(ethenylthiocarbonylmethyl)-azetidin-2-one

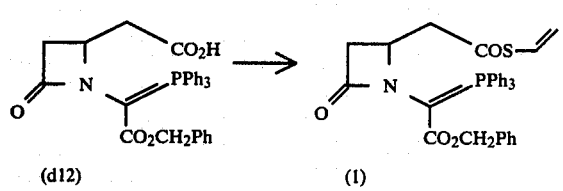

Ethyl vinyl sulphide (prepared according to L. Brandsma Recueil., 1970, 89, 593) (1.75 g) was added cautiously to a stired solution of lithium (0.28 g) in liquid ammonia (17 ml). A vigorous reaction occurred and the compound was added until the blue colour had been discharged. The ammonia was evaporated at 40° and the last traces removed under reduced pressure. Ice water (15 ml) and peroxide-free ether (15 ml) were added and the mixture stirred until all the solid had dissolved. The mixture was cooled to −5° and a cold (−30°) solution of 20% $H_2SO_4$ was added until the solution was slightly acid (no more than pH 4 using a pH stat). The ethereal layer was extracted as quickly as possible and the aqueous phase separated with a further quantity of ether (15 ml). The solution was dried over $MgSO_4$ at −15°.

Sodium metal (0.27 g; based on 60% yield of ethene thiol) was added to ethanol (20 ml) and the metal allowed to dissolve. The ethereal solution of ethene thiol was added to the sodium ethoxide solution at 0° and the mixture allowed to reach R.T. The solvent was evaporated and the residue dissolved in toluene and re-evaporated to yield an off-white solid.

The phosphorane-acid (d12) (2.14 g) and $Et_3N$ (0.414 g) in dry THF (60 ml) were stirred at R.T. and a solution of diethyl phosphorochloridate (0.76 g) in THF (10 ml) was added dropwise under argon and stirred for 3 hours at R.T. To the solution was added the crude ethenethiolate (500 mg) and the mixture stirred at R.T. for half an hour. The solvent was evaporated and the residue chromatographed on silica gel using ethyl acetate to yield the crude product (approx. 1½ g.). Rechromatography on silica gel using ethyl acetate/petrol (bp 60°–80°) gave the product (1) as an oil (0.44 g; 19%). $\nu_{max}$ ($CHCl_3$) 1745, 1690, 1620 cm$^{-1}$.

(b) Preparation of Benzyl 3-Ethenylthio-7-oxo-1-azabicyclo[3.2.0]hept-2-ene-2-carboxylate

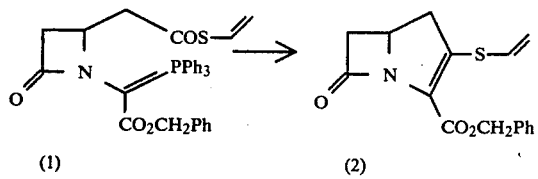

The phosphorane (1) (430 mg) was dissolved in dry toluene (20 ml) and the toluene evaporated to remove traces of water from the starting phosphorane. The gum was redissolved in dry toluene (50ml) and the solution degassed under low vacuum for ten minutes. The solution was refluxed under argon for seven hours. The solvent was evaporated and the residue chromatographed on florisil (200–300 U.S. mesh) using ethyl acetate/petrol (bp 60°–80°) as eluant and slight pressure. The product (2) was collected as an oil (19 mg; 8.5%) which crystallised from benzene/petrol (bp 60°–80°) as a white microcrystalline solid (mp 107°–110°) $\lambda_{max}$ (EtOH) 323 nm ($\epsilon$ 13,800) $\nu_{max}$ ($CHCl_3$) 1785, 1705cm$^{-1}$. $\delta$ppm ($CDCl_3$) 2.85 (1H, dd, J17, 3 Hz, C6-H, trans), 3.05 (2H, brm, C4-$CH_2$), 3.40 (1H, dd, J17, 6 Hz, C6-H, cis), 4.15 (1H, m, C5-H), 5.23 (2H, s, $CO_2CH_2Ph$), 5.44 and 5.54 (2H, two doublets J=10 Hz and J 16 Hz respectively, $H_b$ and $H_a$ in

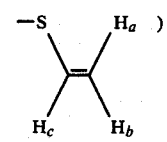

6.47 (1H, dd, J=16, 10 Hz, $H_c$ in

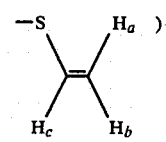

7.25 (5H, br.m, $CO_2CH_2\underline{Ph}$). (Found: C, 63.66; H, 5.05; N, 4.60%; M, 301.0813. $C_{16}H_{15}NO_3S$ requires C, 63.79; H, 4.98; N, 4.65%, M, 301.0773).

The concentrations of this compound required to inhibit the growth of the following bacteria are given below.

| Organism | μg/ml (agar) |
| --- | --- |
| B. subtilis | 10 |
| E. coli 0111 | 20 |
| Kleb. aerogenes A | 10 |
| P. mirabilis C977 | 100 |
| Salmonella typhimurium CT10 | 10 |
| Shigella sonnei MB 11967 | 10 |
| Staph. aureus Russell | 100 |
| Strep. pneumoniae | <2.5 |
| Strep. pyogenes CN10 | <2.5 |

EXAMPLE 2

Preparation of Benzyl 3-(Z-2-(Ethoxycarbonyl)ethenylthio]-7-oxo-1-azabicyclo[3.2.0]hept-2-ene-2-carboxylate

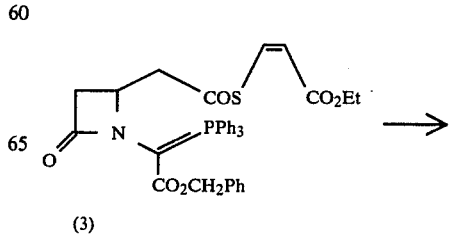

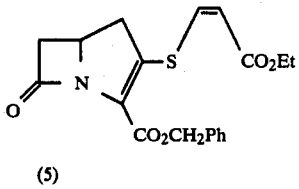

(5)

The phosphorane (3) (400 mg) in dry toluene (400 ml), was degassed and heated to reflux under argon. A Dean and Stark trap was incorporated into the apparatus. Rapid chromatography on silica gel (10 g) eluting with 50% ethyl acetate in petroleum ether gave the bicyclic product (5). This was initially obtained as a gum (9.5 mg), which crystallised on trituration with ether. These crystals (5.4 mg) had mp 100°-102°; $\nu_{max}$ (CHCl$_3$) 1785, 1700 cm$^{-1}$, $\lambda_{max}$ (ethanol) 335 nm ($\epsilon$=21,700). $\delta$ ppm (CDCl$_3$) 1.33 (3H, t, J 7 Hz, CH$_3$), 2.98 (1H, dd, J 3 Hz, 17 Hz, C6-H), 3.09 (1H, dd, J 18 Hz, 9 Hz, C4-H), 3.40 (1H, dd, J 18 Hz, 9 Hz, C4-H), 3.52 (1H, dd, J 17 Hz, 5 Hz, C6-H), 4.25 (2H, q, J 7 Hz, CH$_2$CH$_3$), 3.93-4.43 (1H, partially obscured m, C5-H), 5.30 (2H, s, CH$_2$Ph), 5.95 (1H, d, J 11 Hz cis=CHCO$_2$Et), 7.18 (1H, d, J 11 Hz, cis SCH=CH); 7.25-7.64 (5H, Ar).

The concentrations of this compound required to inhibit the growth of the following bacteria are given below:

| Organism | μg/ml (agar) |
| --- | --- |
| B. subtilis | 20 |
| E. coli 0111 | 100 |
| Kleb. aerogenes A | 100 |
| Salmonella typhimurium | 100 |
| Serratia marcescens US20 | 100 |
| Staph. aureus Oxford | 100 |

EXAMPLE 3

Preparation of Benzyl 3-(E-2-(Ethoxycarbonyl)ethenylthio)-7-oxo-1-azabicyclo[3.2.0]hep-2-ene-2-carboxylate

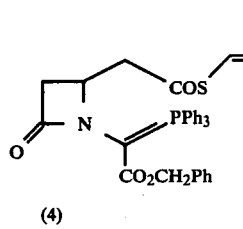

(4)

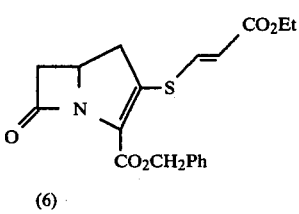

(6)

The phosphorane (4) (254 mg) in dry toluene (250 ml) was degassed and heated to reflux under argon; a Dean and Stark trap was incorporated into the apparatus. After 1 hour the yellow solution was cooled and the solvent evaporated. Rapid chromatography on silica gel (10 g), eluting with 30% ethyl acetate in petroleum ether (60°-80°), gave the bicyclic product (6), as a white solid (8.7 mg). Trituration with ether gave white crystals (5.7 mg) mp 105°-109°; $\nu_{max}$ (CHCl$_3$) 1785, 1700 cm$^{-1}$, $\lambda_{max}$ (ethanol) 332 nm ($\epsilon$ 18,500). $\delta$ ppm (CDCl$_3$) 1.20 (3H, t, 7 Hz, CH$_3$), 2.97 (1H, dd, J 17 Hz, 3 Hz, C6-H, 2.92-3.67 (3H, complex pattern, C4-CH$_2$ and C6-H), 4.18 (2H, q, J 7 Hz, CH$_2$CH$_3$), 3.92-4.45 (1H, m, C5-H), 5.28 (2H, s, CH$_2$Ph), 6.06 (1H, d, J 16Hz, trans CH=CHCO$_2$Et), 7.27-7.45 (5H, Ar), 7.70 (1H, d, J 16 Hz, trans SCH=CH), (Found: C, 61.51; H, 5.02; N, 3.51%. C$_{19}$H$_{19}$NO$_5$S requires C, 61.13; H, 5.09; N, 3.75%).

The preparation of the phosphoranes used in examples (2) and (3)

(a) Preparation of the sodium thiolate (NaSCH=CH—CO$_2$CH$_2$CH$_3$)

Addition of sodium hydrogen sulphide to ethyl propiolate according to the method of Haefliger and Petrizilka (Helv.Chim.Acta., 1966, 49, 1937) gave the sodium salt of ethyl $\beta$-mercaptoacrylate as an amorphous solid (52%), $\nu_{max}$ (KBr) 1680, 1550 cm$^{-1}$; $\delta$ppm (D$_2$O) 1.20 (3H, t, J 7 Hz), 4.19 (2H, q, J 7 Hz), 5.96 (d, J cis 10 Hz) and 6.00 (d, J trans 15 Hz), (1H); 8.10 (d, J cis 10 Hz) and 8.60 (d, J trans 15 Hz) (1H). The ratio of E to Z isomers was 1.3:1.

(b) Preparation of 1-(1-Benzyloxycarbonyl-1-triphenylphosphoranylidenemethyl)-4-[2-(ethoxycarbonyl)ethenyl thiocarbonylmethyl]azetidin-2-one. (Z and E) isomers)

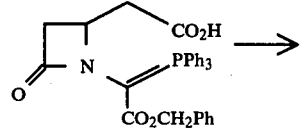

(d12)

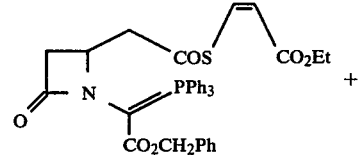

(3)

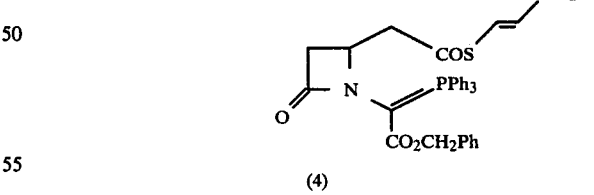

(4)

The phosphorane-acid (d12) (268 mg) in dry tetrahydrofuran (10 ml), under argon, was treated with triethylamine (76 mg) followed by diethylphosphorochloridate (130 mg) diluted with tetrahydrofuran (5 ml). After stirring at room temperature for 3 hours, the sodium salt of ethyl $\beta$-mercaptoacrylate (69 mg) was added in one portion and the mixture stirred for a further 2 hours. The orange mixture was diluted with ethyl acetate (250 ml), washed with water, then brine, dried over magnesium sulphate, filtered and evaporated, to an orange gum (237 mg). Chromatography on silica gel (15 g)

eluting with 50% to 70% ethyl acetate in petroleum ether (60°–80°) almost completely separated the Z (3) and E (4)-isomers of the required thioester.

The Z-isomer (3) was initially obtained as a foam (60 mg), which crystallised from ether (40 mg). The pale yellow crystals were dried under vacuo at 70° for 5 hours, m.p. 132°–134°, $\nu_{max}$ (CHCl$_3$) 1740, 1700, 1615 (broad) cm$^{-1}$. δ ppm (CDCl$_3$) 6.08 (1H, d, J 10 Hz, cis CH=CHCO$_2$Et). (Found: C, 68.31; H, 5.46; N, 2.00. C$_{37}$H$_{34}$NO$_6$PS requires C, 68.19; H, 5.26; N, 2.15%).

The E-isomer (4) was initially obtained as a gum (47.8 mg) which crystallised from ether (25.6 mg). Recrystallisation from ethyl acetate/petroleum ether (60°–80°) gave pale yellow crystals which were collected, washed with ether and dried under vacuo at 70° for 5 hours. m.p. 129°–131.5°, $\nu_{max}$(CHCl$_3$) 1740, 1720, about 1700 (shoulder), 1685 (slight shoulder), 1620 (broad). δ ppm (CDCl$_3$) 6.08 (1H, d, J 16 Hz, trans CH=CHCO$_2$Et), 8.10 (1H, d, J 16 Hz, trans SCH=CH) (Found: C, 68.21; H, 5.52; N, 2.10; C$_{37}$H$_{34}$NO$_6$PS requires C, 68.19; H, 5.26; N, 2.15%).

EXAMPLE 4 p-Nitrobenzyl 3(Z-2-Acetamidoethenylthio)-7-oxo-1-azabicyclo[3,2,0-]hept-2-ene-2-carboxylate

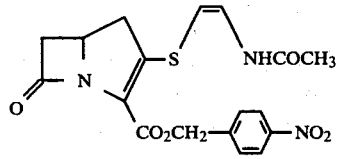

(i) Preparation of Tritylthioacetaldehydediethylacetal

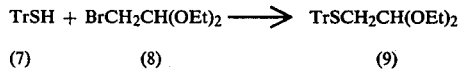

Sodium (0.46 g) was dissolved in absolute alcohol (50 ml) and tritylthiol (7) (5.52 g) was added followed by bromoethyldiethylacetal (8) (4 g). The mixture was refluxed for three hours, filtered and the solvent evaporated. The residue was re-evaporated from toluene and chromatographed on Merck Keiselgel 60 (<230 mesh) using petrol (60°–80°)/ethyl acetate as eluant. The product (9) was obtained as an almost colourless oil (6.5 g; 83%), $\nu_{max}$(CHCl$_3$) 1600, 1495, 1450, 1120, 1060 cm$^{-1}$. δ ppm (CDCl$_3$) 1.16 (3H, t, J 8 Hz, CH$_3$), 2.51 (2H, d, J 6 Hz, CH$_2$CH), 3.44 (4H, m, CH$_2$'s), 4.18 (1H, t, 6 Hz, CH$_2$CH). 7.40 (15H, m, Tr).

(ii) Preparation of Z-2-Acetamido-1-tritylthioethene

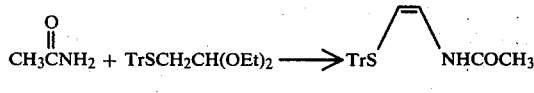

Tritylthioacetaldehydediethylacetal (9) (5 g) was dissolved in benzene (100 ml) and acetamide (10) (4 g) was added. The mixture was heated with stirring to dissolve as much of the acetamide as possible. The mixture was cooled and p.t.s.a. monohydrate (1.5 g) was added. The reaction mixture was then heated under reflux with removal of water for 1½ hours. The solvent was evaporated and the residue chromatographed on Merck Keiselgel 60 (<230 mesh) to yield Z-2-acetamido-1-tritylthioethene (11) as a white crystalline solid (400 mg) from ethyl acetate/petrol (60°–80°) m.p. 154° $\nu_{max}$ (CHCl$_3$) 3400, 1695, 1625, 1260 cm$^{-1}$. δ ppm [(CD$_3$)$_2$CO] 1.97 (3H, s, COCH$_3$) 4.90 (1H, d, J 8 Hz, TrSCH=), 6.88 (1H, dd, J 11, 8 Hz, NHCH=, collapses to a doublet (J 8 Hz) on D$_2$O exchange), 7.32 (15H, s, Tr), 2.45 (1H, br. signal, NH [exchangeable]), $\lambda_{max}$(EtOH) 262 nm. (Found: C, 76.50; H, 5.84; N, 3.76, C$_{23}$H$_{21}$NOS requires C, 76.88; H, 5.85; N, 3.90%).

(iii) Preparation of Silver Z-2-Acetamido-1-ethenylthiolate

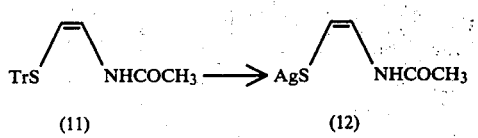

Z-2-Acetamido-1-triphenylmethylthioethene (11) (72 mg) was dissolved in methanol (10 ml) and silver nitrate (34 mg) in methanol (2 ml) was added together with pyridine (16 mg). The mixture was stirred at RT overnight and the yellow precipitate collected by centrifugation. It was washed once with methanol and once with ether and dried to give (12) as a yellow powder (41 mg). $\nu_{max}$ (nujol mull) 3300, 1675, 1625 cm$^{-1}$.

(iv) Preparation of 1-(1-p-Nitrobenzyloxycarbonyl-1-triphenylphosphoranylidenemethyl)-4-(Z-2-acetamidoethenylthiocarbonylmethyl)azetidin2-one

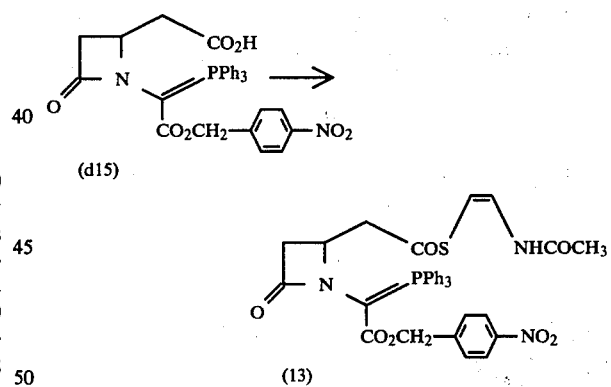

The phosphorane acid (d15) (0.873 g) was dissolved in dry CHCl$_3$ containing DMF (4 drops). Thionyl chloride (0.18 g) was added in dry CHCl$_3$ (6 ml). The mixture was stirred at RT for 2 hours and cooled to −20°. 2,6-Lutidine (0.165 g) was added and the acid chloride pipetted into a cooled solution (−20°) of silver Z-2-acetamido-1-ethenylthiolate (0.39 g) in dry CHCl$_3$ (20 ml) and stirred at RT for 3 hours. The solution was filtered through Hyflo, washed with saturated sodium bicarbonate solution (2×10 ml) and dried (MgSO$_4$). The solvent was evaporated to yield an oil which after chromatography on Merck Keiselgel 60 (<230 mesh) gave the phosphorane thioester (13) an an oil (300 mg) which crystallised from ethyl acetate/ether m.p. 188°–191°. $\nu_{max}$ (CHCl$_3$) 3400, 1745, 1700, 1635, 1525, 1350 cm$^{-1}$. (Found: C, 63.38; H, 4.70; N, 6.01 C$_{36}$H$_{32}$N$_3$O$_7$SP requires C, 63.44; H, 4.70, N, 6.17%).

(v) Preparation of p-Nitrobenzyl 3(Z-2-Acetamidoethenylthio)-7-oxo-1-azabicyclo[3,2,0-]hept-2-ene-2-carboxylate

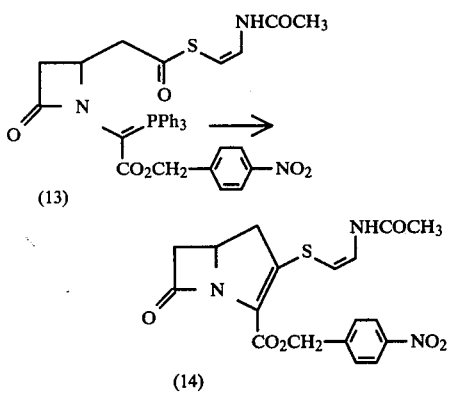

The phosphorane (13) (1 g) was dissolved in dry toluene (1 liter) and refluxed vigorously with removal of water (Dean-Stark) under Argon for 7½ hours. The solvent was evaporated and the residue chromatographed on florisil (200–300 U.S. mesh) using slight pressure to yield the product (300 mg) as an oil contaminated with triphenylphosphine oxide. Trituration of the oil with ether gave the product (14) as a light yellow crystalline solid essentially free of triphenylphosphine oxide (125 mg) m.p. 128°–32°. $\nu_{max}$ (CHCl$_3$) 3375, 1785, 1705, 1635, 1525, 1350 cm$^{-1}$. δppm [(CD$_3$)$_2$CO]. 2.04 (3H, s, COC$\underline{H}_3$), 2.98 (1H, dd, J 3, 17 Hz, C6-Ha) 2.90 to 3.50 (2H, complex pattern, C-4 H$_a$ and H$_b$) 3.46 (1H, dd, J 5.5, 17 Hz, C6-H$_b$) 4.19 (1H, m, C5-H), 5.24 and 5.51 (2H, ABq, J 14 Hz

5.44 (1H, d, J 7 Hz,=C$\underline{H}$-S) 7.26 (1H, dd, J7, 10.5 Hz, NH-C$\underline{H}$=) 7.75 and 8.20 (4H, ABq, J=8.5 Hz,

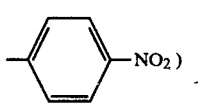

9.00 (1H, brs, NH). $\lambda_{max}$(EtOH) 326, 264, 218 nm.

EXAMPLE 5

Sodium 3-(Z-2-Acetamidoethenylthio)-7-oxo-1-azabicyclo-[3,2,0]hept-2ene-2-carboxylate

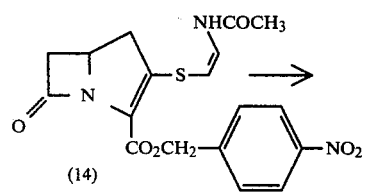

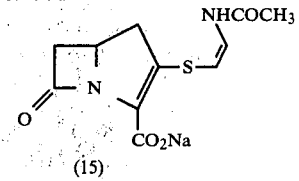

p-Nitrobenzyl 2-(Z-2-acetamidoethenylthio)-7-oxo-1-azabicyclo[3,2,0]hept-2-ene-2-carboxylate (14) (0.075 g) was dissolved in 30% aq. dioxan (12 ml) containing 5% Pd/C (0.095 g) which had been prehydrogenated for 20 minutes. The solution was hydrogenated at ambient temperature and pressure for two hours. The solution was treated with NaHCO$_3$ (0.020 g) in water (2 ml) and filtered through keiselguhr. The dioxan was removed under reduced pressure (to the cloud point) and the aqueous phase extracted with ethyl acetate (3×10 ml). The light yellow aqueous phase was evaporated to low volume (approx. 3 ml) under high vacuum, loaded onto a biogel P2 column and eluted with water containing 1% butanol. The fractions were collected in 10 ml portions and the sodium salt was collected in fractions 8 and 9. Evaporation of the solution gave the product (15) as an off-white solid (0.018 g)$\nu_{max}$ (KBr) 1755 cm$^{-1}$. $\lambda_{max}$ (EtOH) 305, 238 nm.

The concentrations of this compound required to inhibit the growth of the following bacteria are given below.

| Organism | μg/ml (DST agar + 10% Horse Blood). |
|---|---|
| Citrobacter freundii E8 | 12.5 |
| E. coli 0111 | 1.2 |
| K. aerogenes A | 1.2 |
| P. mirabilis C977 | 1.2 |
| P. morganii 1580 | 2.5 |
| S. typhi CT10 | 1.2 |
| Serratia marcescens US20 | 25.0 |
| Shigella sonnei MB 11967 | 1.2 |
| B. subtilis A | 0.5 |
| Staph. aureus Russell | 12.5 |
| Strep. faecalis I | 12.5 |
| Strep.pyrogenes CN10 | 0.5 |

EXAMPLE 6

Benzyl 3(E-2-Acetamidoethenylthio)-7-oxo-1-azabicyclo-[3,2,0]hept-2-ene-2-carboxylate

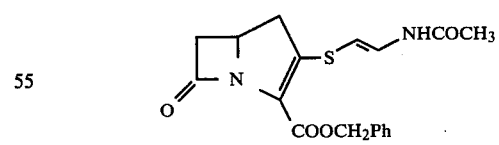

(i) Preparation of Z-2-Acetamidoethenylthio-acetate

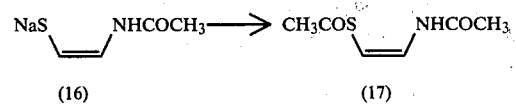

To acetic anhydride (0.62 g) in the dry tetrahydrofuran (50 ml) at 0° under argon was added the sodium thiolate (16) (1.2 g, prepared as in Example 12 (iii)). The mixture was stirred for 16 hours, filtered and the solvent was removed under reduced pressure. Chromatography on silica eluting with chloroform/ethanol mixtures gave the cis-S-acetate (17) (0.57 g) as needles m.p. 110°–114° (benzene) having $\lambda_{max}$ (EtOH) 260 ($\epsilon$12,600) nm; $\nu_{max}$ (CHCl$_3$) 3400, 2950, 1700, 1635, 1470, 1255 and 1120 cm$^{-1}$; $\delta$(CDCl$_3$) 2.12 (3H, s, NOCH$_3$), 2.40 (3H, s, SCOCH$_3$), 5.65 (1H, d, J 8 Hz=CH-S), 7.25 (1H, dd, J 8, 11 Hz), and 7.70 (1H, br, NH). (Found: C, 45.55; H, 5.65; N, 8.65. C$_6$H$_9$NO$_2$S requires C, 45.3; H, 5.65; N, 8.8%).

(ii) Preparation of E-2-Acetamidoethenylthioacetate

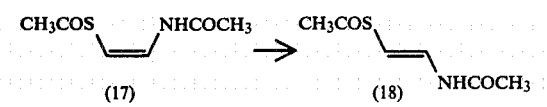

To the ester (17) (0.5 g) in benzene (5ml) at 50° was added diazobicycloundecane (3 drops). After heating for 3 hours under argon, the mixture was cooled, cis-Amide (17) (0.11 g) crystallised out, and the solution obtained after filtration was chromatographed on silica eluting with chloroform/ethanol mixtures to give cis-amide (17) (0.135 g) and trans-amide (18) (0.315 g) m.p. 136°–140° (benzene - pet. ether) having $\lambda_{max}$ (EtOH) 259 ($\epsilon$12,000) nm; $\nu_{max}$ (CHCl$_3$) 3350, 3000, 1695, 1635, 1490, 1265 and 1120 cm$^{-1}$; $\delta$(CDCl$_3$) 2.10 (3H, s, CH$_3$CON), 2.37 (3H, s, CH$_3$COS), 6.0 (1H, d, J 14 Hz, S-CH=), 7.23 (1H, dd, J 11, 14Hz, N-CH=), and 4.43 (1H, br, NH). (Found: C, 45.5; H, 5.80; N, 8.75. C$_6$H$_9$NO$_2$S requires C, 45.3; H, 5.65; N, 8.8%).

(iii) Preparation of 1-(1-Benzyloxycarbonyl-1-triphenylphos-phoranylidenemethyl)-4-(E-2-acetamidoethenythiocarbonylmethyl)azetidin-2-one

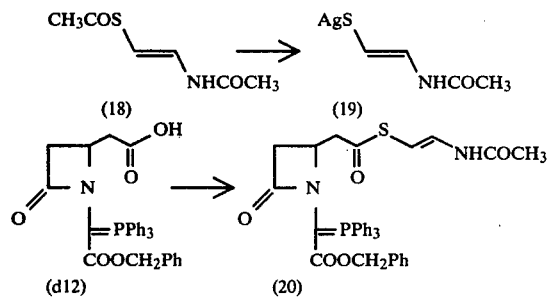

To the trans-amide (18) (1.0 g) in methanol (20 ml) was added a solution of silver nitrate (1.16 g) and pyridine (0.5 ml) in methanol (50 ml). After stirring for 18 hours the mixture was centrifuged and the solid washed once with methanol and once with ether and then dried under vacuum to give the silver thiolate (19) as an orange solid having $\nu_{max}$ (mull) 3350, 1665 and 1635 cm$^{-1}$.

To the acid (d12) (0.535 g) in dry acetonitrile (15 ml) and dimethylformamide (5 drops) was added thionyl chloride (0.075 ml). After stirring for 3 hours under argon, pyridine (0.0835 ml) was added followed by finely ground silver thiolate (19) (0.35 g). After 45 minutes the mixture was filtered, the solvent removed under reduced pressure and the residue was chromatographed on silica eluting with ethyl acetate to give the phosphorane (20) (0.45 g) as needles (ex. ether) having $\lambda_{max}$ (EtOH) 259 nm, $\nu$max (CHCl$_3$) 3450, 3270, 3000, 1745, 1690, 1635 and 1280 cm$^{-1}$. (Found: C, 67.25; H, 5.2; N, 4.25. C$_{30}$H$_{33}$N$_2$O$_5$PS.½ H$_2$O requires C, 67.0; H, 5.25; N, 4.35%).

(iv) Preparation of Benzyl 3(E-2-Acetamidoethenylthio)-7-oxo-1-azabicyclo[3.2.0-]hept-2-ene-2-carboxylate

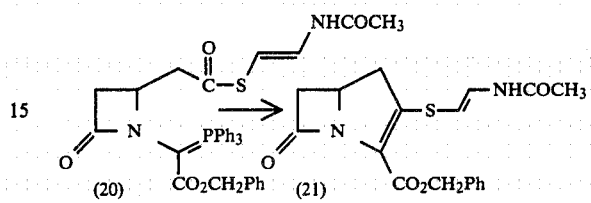

The thioester-phosphorane (20) (0.07 g) was dissolved in dry toluene (100 ml), degassed under low vacuum and heated under reflux vigorously, under argon, for fifteen hours. The solution was cooled and the solvent evaporated. The residue was chromatographed on florisil (200–300 U.S. mesh) to yield the starting phosphorane and the product (23) as a mixture. Re-chromatography of this mixture on Merck Kieselgel 60 using chloroform as eluant grading to 10% ethanol/chloroform gave the product (23) (0.006 g) partially contaminated with starting phosphorane. The product (21) showed $\lambda_{max}$ (EtOH) 324 nm.$\nu_{max}$ (CHCl$_3$) 3300, 1780, 1695, 1625 cm$^{-1}$.

EXAMPLE 7

Benzyl 3-(Z-2-Methoxycarbonylaminoethenylthio-7-oxo-1-azabicyclo-[3.2.0]hept-2-ene-2-carboxylate

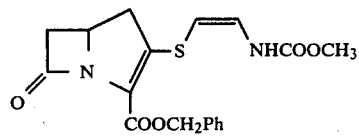

(i) Preparation of 1-(1-Benzyloxycarbonyl-1-triphenylphos-phoranylidenemethyl)-4-(Z-2-methoxycarbonylaminoethenylthiocarbonylmethyl)-azetidin-2-one

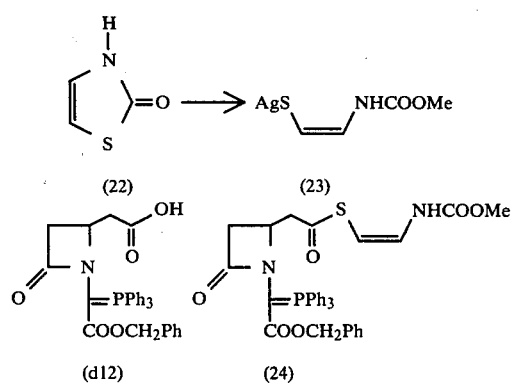

To 2(3H)-thiazolone (22) (0.5 g) (prepared by the method of R. Dahlbom, S. Gronowitz and B. Mathiasson, Acta Chem. Scand. 17, 2479 (1963)) in dry methanol (5 ml) was added to a solution of silver nitrate (0.85 g) and pyridine (0.4 ml) in methanol (37.5 ml). After stirring for 18 hours the solution was centrifuged and the solid was washed with methanol and then with ether to give the thiolate (23) (0.25 g). More thiolate was obtained from the methanol solution. The methanol was removed under vacuum and the solid obtained was washed with ether (30 ml) and then with water (30 ml). The resulting solid was filtered off and dried in vacuo to give thiolate (23) (0.62 g). This gave a total yield of 0.87 g of thiolate (23) having $v_{max}$ (KBr) 3400, 1705, 1630, 1515 and 1385 cm$^{-1}$.

To the acid (d12) (0.645 g) in dry acetonitrile (15 ml) and dimethylformamide (5 drops) was added thionyl chloride (0.09 ml). After stirring for 2 hours under argon, pyridine (0.1 ml) was added as followed by silver thiolate (23) (0.43 g). After 1 hour the mixture was filtered and the solvent removed under reduced pressure. The product was dissolved in ethyl acetate (50 ml) and water (50 ml). The organic layer was washed with saturated sodium bicarbonate solution (30 ml) and brine (30 ml); each aqueous extract being washed once with ethyl acetate (30 ml). The combined organic extracts were dried (MgSO$_4$) and the solvent removed under reduced pressure. Chromatography on florisil eluting with ethyl acetate - pet. ether mixtures and then on silica eluting with chloroformethanol mixtures gave the phosphorane (24) (0.39 g) as a glass m.p. 75°–77° (ex ethyl acetate—pet. ether) having $v_{max}$ (CHCl$_3$) 3430, 3000, 1740, 1695, 1640, 1480, 1440, 1220 and 1100 cm$^{-1}$.

(ii) Preparation of Benzyl 3-(Z-2-Methoxycarbonylaminoethenyl-thio)-7-oxo-1-azabicyclo[3,2,0]-hept-2-ene-2-carboxylate

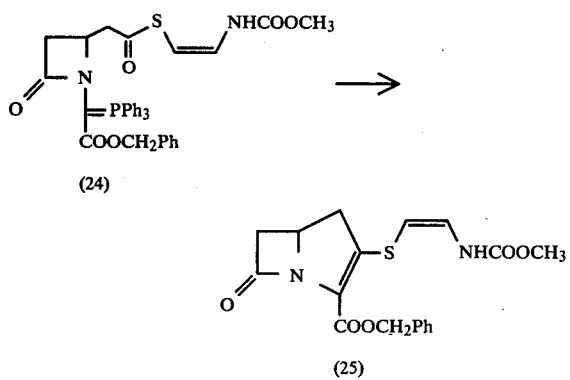

The phosphorane (24) (0.09 g) was dissolved in dry toluene (125 ml) and the solution was degassed under low vacuum. The solution was then heated at reflux under argon for 16 hours. Removal of solvent and chromatography on florisil eluting with 1:1 pet. ether-ethyl acetate gave the product (25) (0.012 g) having λ$_{max}$ (ether) 318 nm, $v_{max}$ (CHCl$_3$) 3420, 2970, 1785, 1735, 1640 and 1480 cm$^{-1}$, δ (CDCl$_3$) 2.87 (1H, dd, J3, 17 Hz, C6-H$_a$), 2.92 (1H, dd, J9, 17 Hz, C4-H$_a$), 3.04 (1H, dd, J9, 17 Hz, C4-H$_b$), 3.44 (1H, dd, J6, 17 Hz, C6-H$_b$), 3.75 (3H, s, CH$_3$), 4.14 (1H, ddt, J3, 6, 9 Hz, C5-H), 5.26 (2H, s, CH$_2$Ph) obsδ~5.22 (1H, d, J <8 Hz, S-CH=), 7.11 (1H, d, J 6 Hz=CH-N) probably obs 7.14 (1H, s, N-H) and 7.32 (5H, m, Ph).

EXAMPLE 8 p-Nitrobenzyl 3(E-2-Acetamidoethenylthio)-7-oxo-1-azabicyclo[3,2,0-]hept-2-ene-2-carboxylate

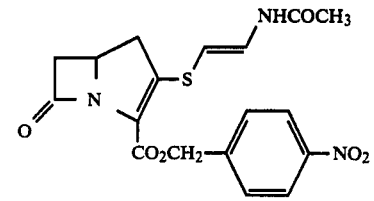

(i) Preparation of E-2-Acetamido-1-tritylthioethene

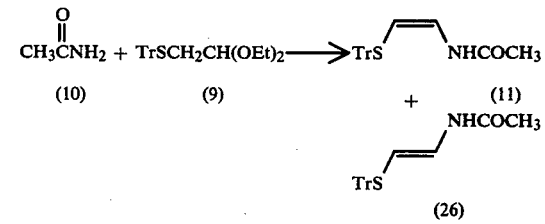

Tritylthioacetaldehydediethylacetal (9) (15.7 g), acetamide (11.8 g) and p.t.s.a. monohydrate (7.6 g) were dissolved in DMF (30 ml) and heated at 90° for three hours. The solvent was evaporated under high vacuum and re-evaporated from toluene. The residue was chromatographed on Merck Keiselgel 60 (<230 mesh) to yield Z-2-acetamido-1-tritylthioethene (11) (3g) and E-2-acetamido-1-trithylthioethene (26) (4g) as a white solid by trituration with ethyl acetate m.p. 192°–194°$v_{max}$ (CHCl$_3$) 1695, 1625, 1490, 1260 cm$^{-1}$. δppm [(CD$_3$)$_2$CO] 1.83 (3H, s, COCH$_3$), 5.24 (1H, d, J15 Hz, TrSCH=), 6.84 (H, dd, J15, 9.5 Hz, NHCH=, collapses to a doublet (J15 Hz) and D$_2$O exchange), 7.27 (15H, s, Tr), 10.02 (1H, d, J9.5 Hz, NH [exchangeable]). (Found: C, 76.90; H, 6.14; N, 3.95, C$_{23}$H$_{21}$NOS requires C, 76.88; H, 5.85; N, 3.90%).

(ii) Preparation of Silver E-2-Acetamido-1-ethenylthiolate (Alternative method to Example 6(iii))

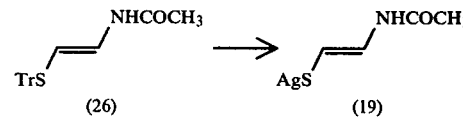

E-2-Acetamido-1-tritylthioethene (26) (1.44 g) was dissolved in methanol (100 ml) by refluxing for 15 minutes. Silver nitrate (0.68 g) in methanol (20 ml) was added together with pyridine (0.32 g) at RT and stirring continued for three hours. The precipitate was collected by centrifugation and washed twice with methanol and once with ether to yield (19) as a dark brown powder (0.425 g) $v_{max}$ (nujol mull) 3220, 1655, 1625 cm$^{-1}$.

(iii) Preparation of 1-(1-p-Nitrobenzyloxycarbonyl-1-triphenylphosphoranylidenemethyl)-4-(E-2-acetamidoethenylthiocarbonylmethyl)azetidin-2-one

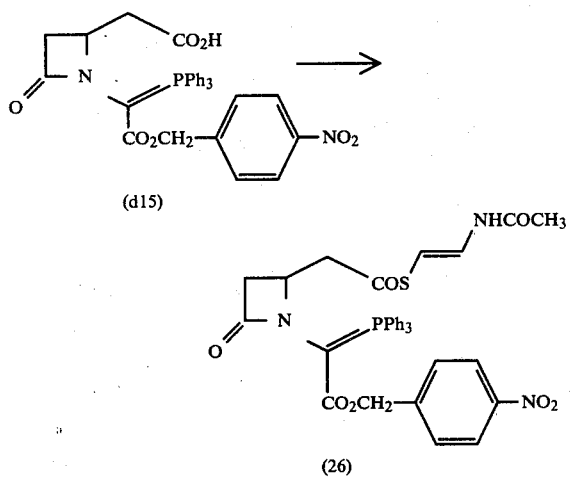

The phosphorane acid (d15) (0.873 g) was dissolved in dry acetonitrile (15 ml) containing DMF (10 drops). Thionyl chloride (0.18 g) was added and the mixture stirred at RT for two hours. Pyridine (0.12 g) was added followed by finely-ground silver E-2-acetamido-1-ethenylthiolate (0.5 g) (19). The reaction was stirred at RT for 45 minutes, filtered and the solvent evaporated. Chromatography of the residue on Merck Keiselgel 60 (<230 mesh) using chlorform/ethanol gave the thioester phosphorane which was further purified by rechromatography on florisil (200–300 U.S. mesh) and chloroform/ethanol as eluant. The product (26) (0.4 g) was obtained a light yellow solid by trituration with ether m.p. 115°–119° . $\nu_{max}$ (CHCl$_3$) 3400, 3375, 1740, 1695, 1625, 1520, 1350 cm$^{-1}$. (Found: C, 62.09; H, 4.68; N, 5.97 C$_{36}$H$_{32}$N$_3$O$_7$SP.H$_2$O requires C, 61.80; H, 4.72; N, 6.01%).

(iv) Preparation of p-Nitrobenzyl 3(E-2-Acetamidoethenylthio)-7-oxo-1-azabicyclo[3,2,0]hept-2-ene-2-carboxylate

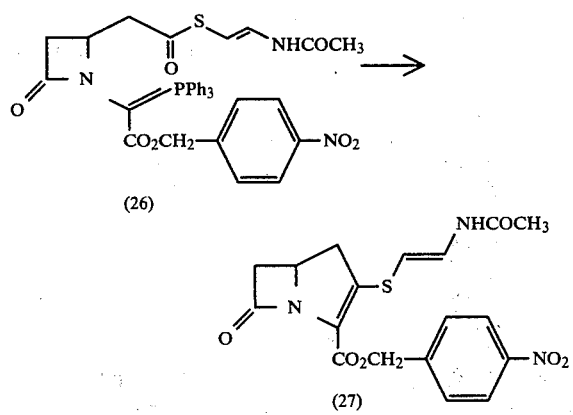

The phosphorane (26) (0.2 g) was dissolved in dry toluene (250 ml) and refluxed vigorously with removal of water (Dean-Stark) for 24 hours under argon. The solvent was evaporated and the residue chromatographed on florisil (200–300 U.S. mesh) using slight pressure and chloroform/ethanol as eluant to yield the starting phosphorane (0.15 g) and as the more polar component the title product (0.018 g; 15%) identical spectroscopically with the previous example.

EXAMPLE 9

Sodium 3(E-2-Acetamidoethenylthio)-7-oxo-1-azabicyclo-[3.2.0]hept-2-ene-2-carboxylate

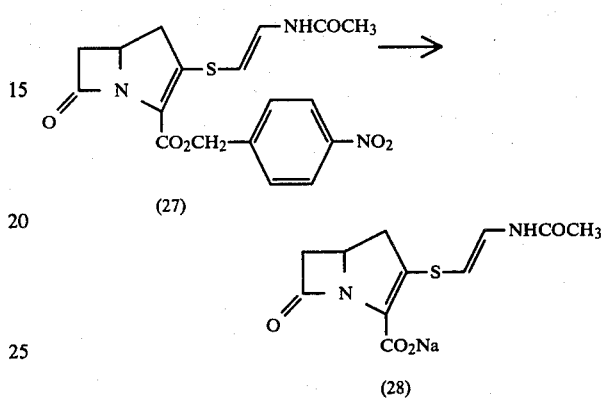

p-Nitrobenzyl 3-(E-2-Acetamidoethenylthio)-7-oxo1-azabicyclo[3.2.0]hept-2-ene-2-carboxylate (27) (0.035 g) was dissolved in 30% aq. dioxan (6 ml) containing 5% Pd/C (0.04 g) which had been prehydrogenated for 20 minutes. The solution was hydrogenated at ambient temperature and pressure for two hours. The solution was treated with NaHCO$_3$ (0.007 g) in water (1 ml) and filtered through keiselguhr. The dioxan was removed under reduced pressure and the aqueous phase extracted with ethyl acetate (3×5 ml). The aqueous phase was evaporated to low volume (approx. 2 ml) under high vacuum, loaded onto a biogel P2 column and eluted with water. The fractions were collected in 10 ml portions and the sodium salt collected in fractions 5, 6 and 7. Evaporation of the solution give the product (28) as a white solid (0.009 g) $\nu_{max}$ (KBr)1750 cm$^{-1}$ $\lambda_{max}$ (EtOH)307, 229 nm.

The concentrations of this compound required to inhibit the growth of the following bacteria are given below.

| Organism | μg/ml (DST agar + 10% Horse Blood). |
|---|---|
| Citrobacter freundii E8 | 3.1 |
| Enterobacter cloacae N1 | 3.1 |
| Escherichia coli O111 | 1.6 |
| Escherichia coli JT39 | 3.1 |
| Klebsiella aerogenes A | 0.8 |
| Proteus mirabilis C977 | 12.5 |
| Proteus morganii 1580 | 12.5 |
| Proteus rettgeri WM16 | 12.5 |
| Proteus vulgaris WO91 | 25 |
| Pseudomonas aeruginosa A | 12.5 |
| Salmonella typhimurium CT10 | 3.1 |
| Serratia marcescens US20 | 6.2 |
| Shigella sonnei MB 11967 | 3.1 |
| Bacillus subtilis A | 3.1 |
| Staphlococcus aureus Oxford | 1.6 |
| Staphlococcus aureus Russell | 12.5 |
| Staphlococcus aureus 1517 | 25 |
| Streptococcus faecalis I | 25 |
| Streptococcus pneumoniae CN33 | 0.2 |
| Streptococcus pyogenes CN10 | 3.1 |

-continued

| Organism | μg/ml (DST agar + 10% Horse Blood). |
|---|---|
| E. coli ESS | ≦0.1 |

EXAMPLE 10

Benzyl 3(Z-2-Acetamidoprop-1-enylthio)-7-oxo-1-azabicyclo[3.2.0]hept-2-ene-2-carboxylate.

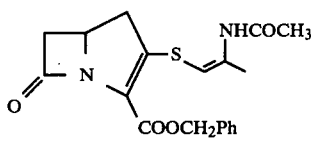

(i) Preparation of 1-(1-Benzyloxycarbonyl-1-triphenylphosphoranylidenemethyl)-4-Z-2-acetamidoprop-1-enylthiocarbonylmethyl)azetidin-2-one.

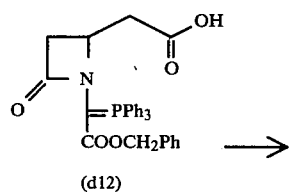

(d12)

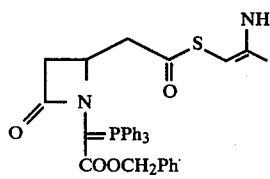

(29)

The phosphorane-acid (d12) (1.072 g) and triethylamine (0.42 ml) in dry THF (50 ml) were stirred at room temperature and a solution of diethyl phosphorochloride (0.52 g) in THF (5 ml) was added dropwise under argon and stirred for 3 hours at R.T. To this solution was added sodium Z-2-acetamidoprop-1-enylthiolate (0.44 g of a 1:1 mixture with NaCl as prepared as described in S. Hoff, A.P. Blok and E. Zwanenburg, Recueil, 92, 879 (1973)) and the mixture was stirred for 45 mins. The solution was poured onto ethyl acetate (100 ml) and brine (100 ml), the aqueous layer was extracted twice more with ethyl acetate (100 ml) and each organic extract was washed once with brine (30 ml). The combined organic layers were dried (Na$_2$SO$_4$) and the solvent was removed under reduced pressure. Chromatography on silica eluting with ethyl acetate gave the phosphorane (29) (0.5 g) as a slightly yellow oil. Further purification by repeat chromatography and crystallization from ether pet.ether gave pure phosphorane (29) as a microcrystalline solid m.p. 84°-87° having ν$_{max}$ (CHCl$_3$) 3350, 3000, 1750, 1695, 1630, 1485, 1240, 1110 and 680 cm$^{-1}$.

(ii) Preparation of Benzyl 3(Z-2-Acetamidoprop-1-enylthio)-7-oxo-1-azabicyclo[3.2.0]hept-2-ene-2-carboxylate

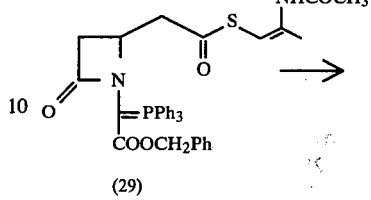

(29)

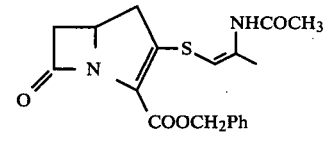

(30)

The phosphorane (29) (0.058 g) was dissolved in dry toluene (120 ml) and the solution was degassed under low vacuum. The solution was then heated vigorously under reflux under argon for 9 hours. Removal of solvent and chromatography on silica eluting with ethyl acetate gave the product (30) (0.01 g) as an oil having ν$_{max}$ (CHCl$_3$) 3400, 3000, 1785, 1705, 1620, 1475 and 1330 cm$^{-1}$; ν$_{max}$(EtOH) 325 nm; δ(CDCl$_3$) 2.08 (3H, s, COCH$_3$), 2.33 (3H, d, J 1 HZ

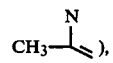

2.89 (1H, dd, J 3, 17 Hz, C6-H$_a$), 2.93 (1H, dd, J9, 18 Hz, C4-H-hd a), 3.05 (1H, dd, J 9, 18 Hz, C4-H$_b$), 3.47 (1H, dd, J 5.5, 17 Hz, C6-H$_b$), 4.18 (1H, ddt, J3, 5.5, 9 Hz, C5-H), 5.11 (1H, br.d, J 1.3 Hz, S-CH=), 5.30 (2H, s, CH$_2$Ph), and 7.45 (signal covered by Ph$_3$PO impurity, Ph and N-H).

EXAMPLE 11 p-Nitrobenzyl 3(Z-2-Acetamidoprop-1-enylthio)-7-oxo-1-azabicyclo-3.2.0]hept-2-ene-2-carboxylate

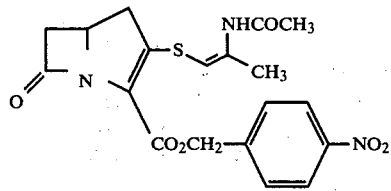

(i) Preparation of 1-(1-p-Nitrobenzyloxycarbonyl-1-triphenylphosphoranylidenemethyl)-4-(Z-2-acetamidoprop-1-enylthiocarbonylmethyl)azetidin-2-one

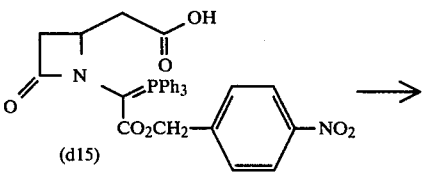

(d15)

-continued

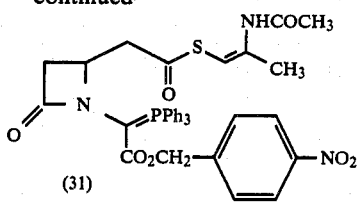
(31)

The phosphorane acid (d15) (0.582 g) and triethylamine (0.101 g) in dry THF (25 ml) were stirred at room temperature and a solution of diethyl phosphorochloridate (0.19 g) in THF (5 ml) was added dropwise under argon and stirred for three hours. Sodium Z-2-acetamidoprop-1-enylthiolate (0.21 g) of a 1:1 mixture with NaCl) was added to the solution and the mixture stirred for half an hour. The solvent was evaporated and the residue dissolved in ethyl acetate (20 ml), washed with saturated NaHCO$_3$ (3×10 ml) and dried (MgSO$_4$). Evaporation of the solvent yielded an oil which was chromatographed on florisil (200–300 U.S. mesh) to give the product (31; 0.325 g) as a light yellow oil. $\nu_{max}$ (CHCl$_3$) 3400, 1745, 1700, 1625, 1615, 1525, 1345 cm$^{-1}$.

(ii) Preparation of p-Nitrobenzyl 3(Z-2-Acetamidoprop1-enylthio)-7-oxo-1-azabicyclo[3.2.0]hept-2-ene-2-carboxylate

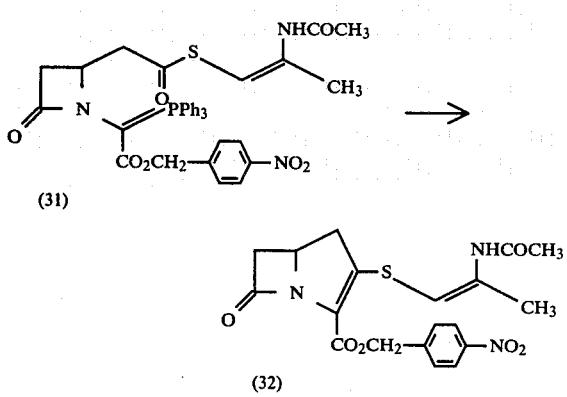

The phosphorane (31) (0.25 g) was dissolved in dry toluene (250 ml) and refluxed vigorously with removal of water (Dean-Stark) for nine hours. The solvent was evaporated and the residue chromatographed on florisil (200–300 U.S. mesh) using slight pressure to yield the product (32)(0.03 g) contaminated with triphenylphosphine oxide as a colourless oil, $\nu_{max}$ (CHCl$_3$) 3375, 3000, 1785, 1710, 1610 cm$^{-1}$, $\lambda_{max}$(EtOH) 327 nm; δ (CDCl$_3$) 2.10 (3H, s, COCH$_3$), 2.34 (3H, d, J 1 Hz, C$\underline{H}_3$), 2.93 (1H, dd, J 3, 17 Hz, C6-H$_a$), 3.00 (2H, m, C4-CH$_2$), 3.50 (1H, dd, J 5.5, 17 Hz, C6-H$_b$), 4.18 (1H, m, C5-H), 5.11 (1H, d, J 1 Hz, S-C=), 5.34 (2H, ABq, J 14Hz,

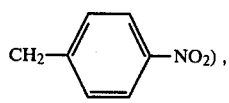

8.20 (1H, part of ABq., J 9 Hz, the other part being obscured by Ph$_3$P=O impurity).

EXAMPLE 12

Benzyl 3(Z-2-Acetamidoethenylthio)-7-oxo-1-azabicyclo[3.2.0]-hept-2-ene-2-carboxylate

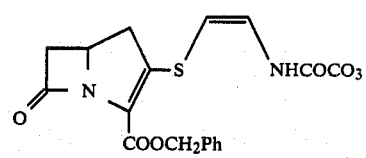

(i) Preparation of 2-(2,2'-Diethoxyethylthio)-acetamide

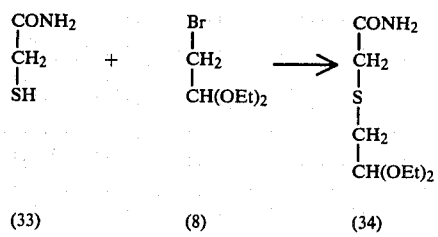

Sodium (0.878 g) was dissolved in absolute ethanol (150 ml) under an inert atmosphere. Thioglycolamide (33) (3.47 g, prepared as described in Sokol and Ritter, J. Amer. Chem. Soc., 70, 3517, 1948) was added and, when practically all the amide had dissolved, bromoacetaldehyde diethyl acetal (8) (11.5 ml) was dropped in. The mixture was heated at 60°–65° for 7 hours and then cooled. The sodium chloride was filtered off and the ethanol was removed under reduced pressure. The residue was dissolved in ethyl acetate (100 ml) and brine (50 ml) and the aqueous layer extracted once more with ethyl acetate (50 ml). The combined organic extracts were dried (Na$_2$SO$_4$) and the solvent removed under reduced pressure to yield an oil. Chromatography on silica eluting with ethyl acetate - pet. ether mixtures gave the amide (34) (6g) as an oil having $\nu_{max}$(CHCl$_3$) 3500, 3400, 3000, 1690, 1125 and 1060 cm$^{-1}$; δ(CDCl$_3$) 1.20 (6H, t, J 7 Hz, CH$_3$), 2.80 (2H, d, J 5 Hz, -CHC$\underline{H}_2$-S), 3.25 (2H, s, -SCH$_2$CO), 3.58 (4H, 2×q, J 7 Hz, -OCH$_2$-), 4.62 (1H, t, J 5 Hz, -C$\underline{H}$CH$_2$S-) and 7.00 (2H, s, CONH$_2$); m/e 207 (M+, 0.2%), 103 (100%, CH(OEt)$_2$+) and 75 (30%, CHOH-(OEt)+); M+, 207.0951. C$_8$H$_{17}$NO$_3$S requires M, 207.0929.

(ii) Preparation of 2,3-Dihydro-4H-1,4-thiazin-3-one

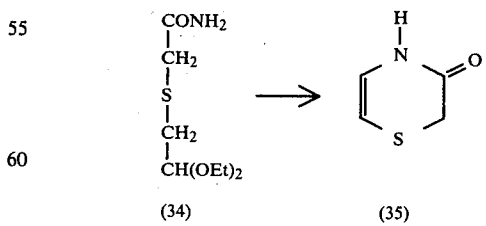

The amide (34) (4 g) was dissolved in benzene (80 ml), p-toluenesulphonic acid (0.01 g) added, and the mixture heated under reflux in an inert atmosphere with a Dean and Stark trap for 3 hours. Removal of solvent and chromatography on silica eluting with pet. ether - ethyl acetate mixtures gave the thiazine (35) as white plates m.p. 74.5°–75° (exethyl acetate- pet.ether) having $\nu_{max}$(CHCl$_3$) 3200, 1690, 1635, 1625, 1380 and 690 cm$^{-1}$, $\nu$(CDCl$_3$) 3.28 (2H, s, CH$_2$), 5.57 (1H, d, J 7 Hz, =CH-S), 6.37 (1H, dd, J 5, 7 Hz, =CH-N), and 9.13 (1H, br, N-H), $\lambda_{max}$(EtOH), 230 ($\epsilon$, 2940) and 302 ($\epsilon$, 2690)nm. (Found: C, 41.4; H, 4.4; N, 12.1. C$_4$H$_5$NSO requires C, 41.7; H, 4.35; N, 12.2%).

(iii) Preparation of 1-(1-Benzloxycarbonyl-1-triphenylphosphoranylidenemethyl)-4-(Z-2-acetamidoethenylthiocarbonylmethyl)azetidin-2-one

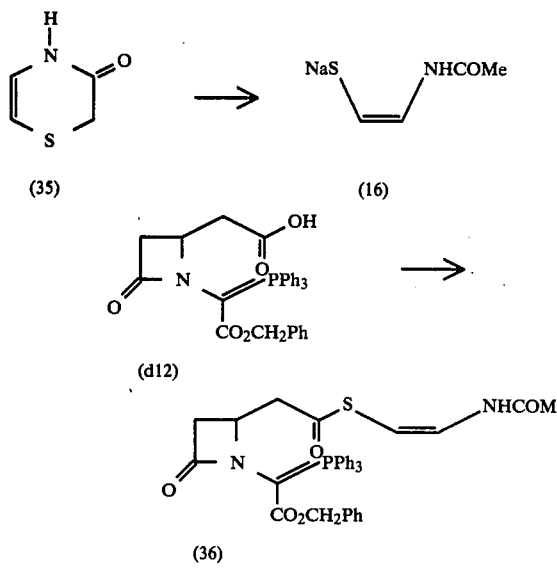

The thiazine (35)(0.575 g) was dissolved in liquid NH$_3$ (20 ml) and to this solution, under argon and with stirring, was added sodium metal (0.23 g). When the blue colour had disappeared, ammonium chloride (0.2675 g) was added. The ammonia was then allowed to evaporate and the last traces removed under vac at 80°. This gave the sodium thiolate (16) as a buff coloured solid.

The phosphorane acid (d12) (1.07 g) and triethylamine (0.42 ml) in dry THF (50 ml) were stirred at room temperature and a solution of diethyl phosphorochloridate (0.52 g) in THF (5ml) was added dropwise under argon. After stirring to 3 hours, the sodium thiolate (16) (0.4 g, 1:1 thiolate - NaCl) was added and the mixture stirred for a further 45 mins. The mixture was poured onto ethyl acetate (100 ml) and brine (100 ml) and the ethyl acetate layer extracted twice with sat. NaHCO$_3$ solution (50 ml); each aqueous layer being re-extracted with ethyl acetate (100 ml). The combined organic layers were dried, and the solvent removed under reduced pressure. Chromatography twice on silica and once on florisil eluting with pet.ether - ethyl acetate mixtures gave pure phosphorane (0.35 g) as an oil which crystallized on addition of ether to give the phosphorane (36) (0.28 g) m.p. 179–183, having $\nu_{max}$(CHCl$_3$)3400, 3250, 3000, 1745, 1700, 1635 and 1110 cm$^{-1}$. (iv) Preparation of Benzyl 3(Z-2-Acetamidoethenylthio)-7-oxo-1-azabicyclo[3.2.0-]hept-2-ene-2-carboxylate

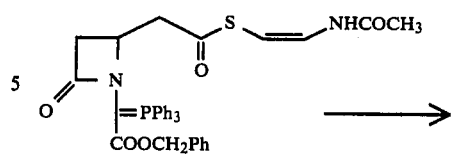

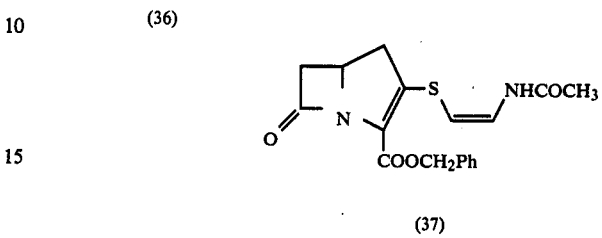

The phosphorane (36) (0.06 g) was dissolved in dry toluene (100 ml) and the solution was degassed under low vacuum. The solution was then heated vigorously under reflux under argon for 9 hours. Removal of solvent and chromatography on silica eluting with ethyl acetate gave the product (37) (0.009 g) as a white solid having mp 143°–6° (ex ether); $\nu_{max}$(CHCl$_3$) 3400, 3000, 1790, 1705, 1635 and 1260 cm$^{-1}$; $\lambda_{max}$(EtOH) 325nm; $\delta$(CDCl$_3$) 2.10 (3H, s, COCH$_3$) 2.90 (1H, dd, J 3, 17 Hz, C6-H$_a$), 2.98 (1H, dd, j 9, 18 Hz, C4-H$_a$), 3.07 (1H, dd, J9, 18 Hz, C4-H$_b$), 3.47 (1H, dd, J 6, 17 Hz, C6-H$_b$), 4.18 (1H, ddt, J 3, 6, 9 Hz, C5-H), 5.27 (2H, s, CH$_2$Ph), 5.35 (1H, d, J 9 Hz, S-CH=), 7.35 (6H, m, Ph,obs.=CH-N) and 8.30 (1H, brd, J 13 Hz, N-H).

(iii) Alternative procedure. Preparation of 1-(1-Benzyloxycarbonyl-1-triphenylphosphoranylidenemethyl)-4-(Z-2-Acetamidoethenylthiocarbonylmethyl)-azetidin-2-one using the lithium thiolate.

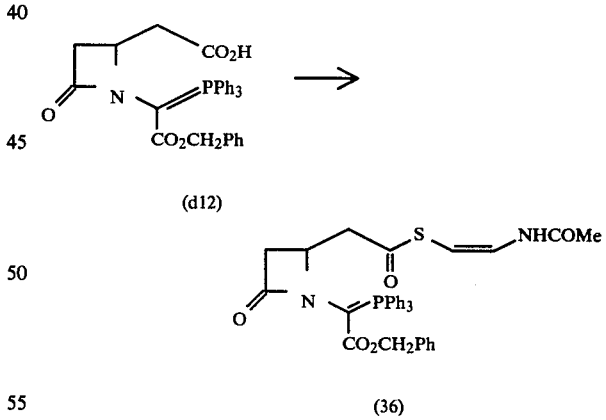

The thiazine (35) (0.575 g) was dissolved in liquid NH$_3$ (20 ml) and to this solution, under argon, with stirring was added lithium metal (0.07 g). When the blue colour had disappeared, ammonium chloride (0.2675 g) was added. The ammonia was then allowed to evaporate and the last traces removed under vacuum to give the lithium thiolate as a white solid.

The phosphorane acid (0.536 g) and triethylamine (0.101 g) were treated with a solution of diethylphosphorochloridate (0.19 g) in THF (5 ml). The reaction was stirred at RT, under argon, for three hours and treated with the lithium thiolate (0.17 g, 1:1 mixture thiolate: LiCl). The mixture was stirred at RT for one hour, the solvent evaporated and the residue chromatographed on Merck Keiselgel 60 (<230 mesh) to yield the product (36) (0.4 g) as a white crystalline solid from ethyl acetate.

EXAMPLE 13

Preparation of p-Nitrobenzyl 3-(2-Phenylethenylthio)-7-oxo-1-azabicyclo[3.2.0]hept-2-ene-2-carboxylate (E- and Z-isomers).

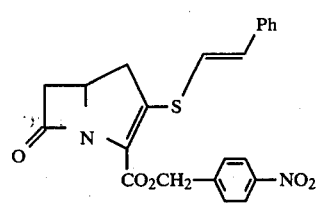

E-isomer

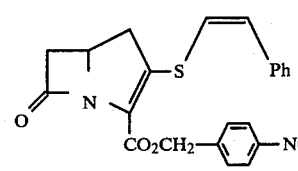

Z-isomer (i) Preparation of silver 2-phenylethenylthiolate

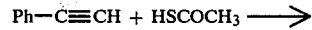

(38)    (39)

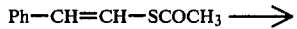

(40)

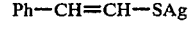

(41)

Phenylacetylene (38) (12 ml) and thiolacetic acid (39) (7 ml) were mixed and left to stand at room temperature overnight. The reaction mixture was dissolved in ethyl acetate (70ml) and washed with N sodium hydroxide solution (1×25 ml) and then brine solution (2×25 ml). Evaporation of the ethyl acetate and residual phenylacetylene (60°/15 mm) left an oil (5 g), shown by NMR to be a mixture (3:1) of Z- and E-isomers of (40) (δ6.90 (d) and 6.53 (d) J 11 Hz; δ 6.93 (d) and 6.60 (d) J 16 Hz in CDCl$_3$). A mixture (3:1) of the isomers of (40)(4 g) was dissolved in methanol (30 ml) and pyridine (1.78 g) was added. The solution was stirred at room temperature while silver nitrate (3.82 g) in methanol (200 ml) was added. After stirring over 48 hours the precipitate was collected, washed with methanol and dried to give (41) as a brown solid (3.9 g).

(ii) Preparation of 1-(1-p-Nitrobenzyloxycarbonyl-1-triphenylphosphoranylidenemethyl)-4-(2-phenylethenylthiocarbonylmethyl)azetidin-2-one.

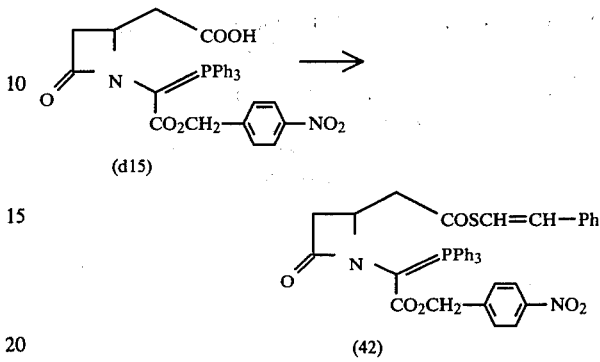

The acid (d15) (0.4 g) was dissolved in acetonitrile (2 ml) and treated with thionyl chloride (0.082 g) and dimethylformamide (2 drops). After stirring at room temperature for 2.5 hours finely powdered silver thiolate (41) (0.25 g) was added and stirring continued for a further 20 hours. The solvent was removed under reduced pressure; ethyl acetate (50 ml) was added and the organic phase washed with saturated sodium bicarbonate solution (25 ml) and then brine (2×25 ml).

The organic phase was dried over magnesium sulphate and then evaporated to dryness, the residue being chromatographed on silica gel 60 (230–400 mesh). Elution with ethyl acetate/60°-80° petroleum ether/ 7:3) gave the product as a mixture of Z- and E-isomers of (42) (0.16g), $\nu_{max}$(CHCl$_3$) 1740, 1695 and 1640 cm$^{-1}$.

(iii) Preparation of p-Nitrobenzyl 3-(2-phenylethenylthio)-7-oxo-1-azabicyclo[3.2.0]hept-2-ene-2-carboxylate.

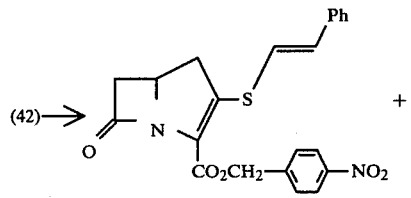

(43) (E-isomer)

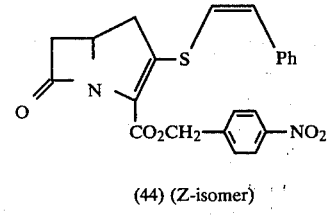

(44) (Z-isomer)

The phosphorane (42) (0.2 g) was dissolved in dry toluene (250 ml) and treated at reflux under argon for 12 hours, with provision for the removal of water (Dean-Stark Trap). The solvent was evaporated under reduced pressure and the residue chromatographed on silica gel 60 (230–400 Mesh) (10 g) eluting rapidly with ethyl acetate/60°-80° petroleum ether (1:1). The first product eluted was the E-isomer (43) (7 mg), $\lambda_{max}$(EtOH) 336 and 265nm, $\nu_{max}$(CHCl$_3$) 1785 and 1710 cm$^{-1}$; δ ppm (CDCl$_3$) 2.90 (1H, dd, J 16 and 3 Hz, C6-H trans), 3.00 - 3.60 (2H, m, C4-H$_2$), 3.50 (1H, dd, J ≠and 6 Hz, C6-H cis), 4.00-4.45 (1H, m, C5-H), 5.25 and 5.50 (2H, ABq, J 13 Hz, CO$_2$C$\underline{H}_2$), 6.56 (1H, d, J 15 Hz, CH═CH trans), 6.95 (1H, d, J 15 Hz, Ch═CH trans), 7.50 (5H, s, Ph), 7.62 (2H, d, J 8 Hz, Ar), 8.20 (2H, d, J 8 Hz, Ar). (Found: M$^+$-42, 380.0808. C$_{20}$H$_{16}$N$_2$O$_4$S requires 380.0829). The more polar Z-isomer (44) (4 mg) showed $\lambda_{max}$(EtOH) 336 and 265nm, $\nu_{max}$(CHCl$_3$) 1785 and 1710 cm$^{-1}$; δppm (CDCl$_3$) 2.97 (1H, dd, J 16 and 3 Hz, C6-H trans), 3.05-3.55 (2H, m, C4-H$_2$), 3.55 (1H, dd, J 16 and 6 Hz, C6-H cis), 4.05-4.45 (1H, m, C5-H), 5.25 and 5.50 (2H, ABq, J 13 Hz, CO$_2$C$\underline{H}_2$), 6.40 (1H, d, J 11 Hz, CH═CH cis), 6.75 (1H, d, J 11 Hz, CH═CH cis), 7.15-7.70 (7H, m, Ph, Ar), 8.20 (2H, d, J 8 Hz, Ar). Further elution of the column with ethyl acetate gave unchanged phosphorane (42) (0.158 g).

EXAMPLE 14

Phthalidyl 3(E-2-Acetamidoethenylthio)-7-oxo-1-azabicyclo[3.2.0]-hept-2-ene-2-carboxylate

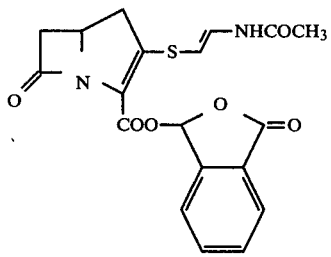

(i) Preparation of 4-Allyl-1-(1-phthalidyloxycarbonyl-1-triphenyl-phosphoranylidenemethyl)azetidin-2-one

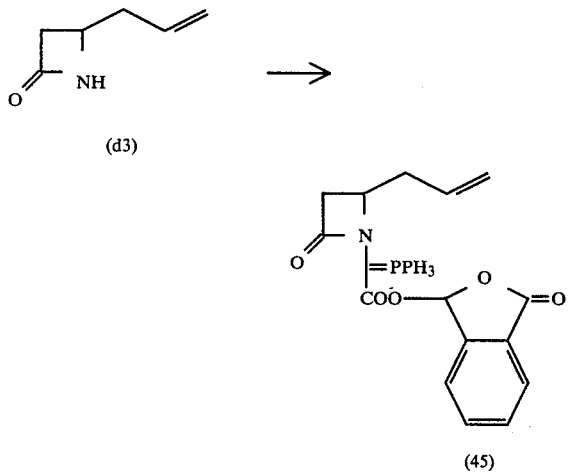

(45)

Allylazetidinone (d3) (6.3 g), glyoxylic acid monohydrate (5.52 g), 30 4A molecular sieves (⅛" pellets) and dry DMF (30 ml) were stirred for four hours at room temperature. The mixture was cooled to 0° and finely powdered potassium carbonate (4.14 g) was added. The mixture was allowed to warm up to room temperature and was stirred for fifteen minutes. The solution was again cooled to 0° and bromophthalide (12.8 g) was added. The resulting solution was stirred for two-and-a-half hours at room temperature and then poured onto $N/10$ hydrochloric acid (250 ml) and ethylacetate (250 ml). The organic extract was washed once more with $N/10$ hydrochloric acid (250 ml) and then with half-saturated sodium hydrogen carbonate (250 ml) and brine (250 ml); each aqueous washing being extracted once with ethyl acetate (100 ml). The combined organic extracts were dried (Na$_2$SO$_4$) and the solvent removed under reduced pressure to give an oil.

A stirred solution of this oil in dry tetrahydrofuran (250 ml), under argon, was cooled to -20°, and treated with 2,6-lutidine (7.6 ml) followed by thionyl chloride (4.8 ml in 30 ml tetrahydrofuran). After stirring for twenty minutes at -20° the mixture was brought to room temperature and filtered. The precipitated solid was washed with toluene and the combined filtrate and washings evaporated to a small volume under reduced pressure. The residue was dissolved in toluene and re-evaporated to dryness twice to remove excess thionyl chloride The oil obtained was dissolved in dry tetrahydrofuran (250 ml) and treated with 2,6-lutidine (7.6 ml) and triphenylphosphine (12 g). After stirring for sixteen hours, the mixture was filtered and the solvent removed from the filtrate under reduced pressure. The filtrant was dissolved up in ethyl acetate (250 ml) and $N/10$ hydrochloric acid (250 ml) and added to the evaporated filtrate. The organic layer was separated and washed with $N/10$ hydrochloric acid (250 ml), water (250 ml), half-saturated sodium hydrogen carbonate (250 ml) and brine (250 ml); each aqueous washing being extracted with ethyl acetate (250 ml). The combined organic extracts were dried (Na$_2$SO$_4$) and the solvent removed under reduced pressure. Chromatography on silica eluting with 1:1 ethyl acetate-pet.ether to ethyl acetate gave the phosphorane (45) (8 g) as a foam which crystallised on addition of ether (6 g); m.p. 182°-195° (ethyl acetate-pet.ether); (Found: C, 72.8; H,5.2; N,2.5. C$_{34}$H$_{28}$NO$_5$P requires C,72.7; H,5.0; N,2.5%).

(ii) Preparation of 1-(1-Phthalidyloxycarbonyl-1-triphenylphosphoranylidenemethyl)-4-carboxymethylazetidin-2-one

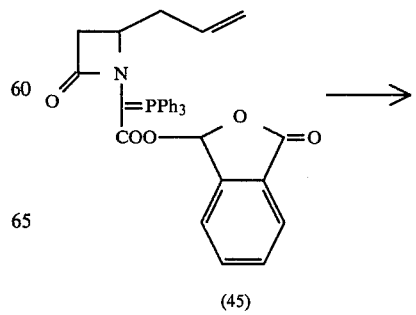

(45)

-continued

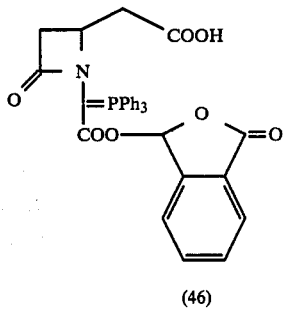

(46)

The phosphorane (45) (1.68 g) was dissolved in a solution of trifluoroacetic acid (18 ml) in dry methylene chloride (90 ml) and left for ten minutes at room temperature. The mixture was cooled to -40° and ozone passed through the solution with stirring until blue. (n.b. trifluoroacetic acid precipitates out of solution so care should be taken to ensure good mixing). Excess ozone was removed by passing argon through the solution at -40° and a solution of m-chloroperbenzoic acid (0.51 g) in methylene chloride (15 ml) was added. The mixture was allowed to reach room temperature slowly and then stirred overnight. The solution was diluted with toluene (50 ml) and reduced in volume to 50 ml under reduced pressure. Excess trifluoroacetic acid was removed by azeotroping twice with toluene (75 ml) and the residue was dissolved in ethyl acetate and chloroform. Chromatography of this mixture on silica eluting with chloroform - ethyl acetate mixtures gave the acid (46) (1.08 g) as a light yellow solid having $\nu_{max}(CHCl_3)$ 3000, 1780, 1740, 1615 and 960 cm$^{-1}$.

(iii) Preparation of 1-(1-Phthalidyloxycarbonyl-1-triphenylphos-phoranylidenemethyl)-4-(E-2-acetamidoethenylthiocar-bonylmethyl)azetidin-2-one

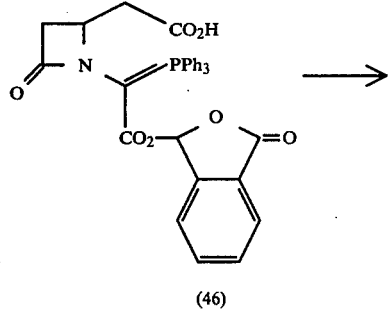

(46)

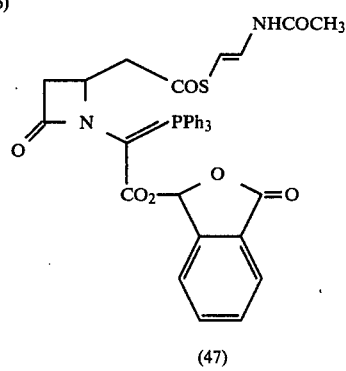

(47)

The phosphorane acid (46) (0.867 g) was dissolved in dry acetonitrile (20 ml) containing DMF (10 drops). Thionyl chloride (0.18 g) was added and the mixture stirred at room temperature for two hours. Pyridine (0.12 g) followed by finely-ground E-2-acetamido-1-ethenylthiolate (0.46 g) (19) was added. The reaction was stirred at room temperature for one hour, filtered through Keiselguhr and the solvent evaporated. The residue was dissolved in dichloromethane (50 ml) and washed with saturated NaHCO$_3$ solution (2×25 ml). The organic phase was dried (MgSO$_4$) and the solvent evaporated. Chromatography of the residue on Merck Keiselgel 60 (<230 mesh) using CHCL$_3$/EtOH as eluant gave the phthalide ester (47) as a white solid by trituration with ether. M.p. 138°-43° $\nu_{max}$ (CHCl$_3$) 3400, 3300, 1740, 1685, 1625 cm$^{-1}$.

(iv) Preparation of Phthalidyl 3(E-2-Acetamidoethenylthio)-7-oxo-1-azabicyclo [3,2,0]hept-2-ene-2-carboxylate

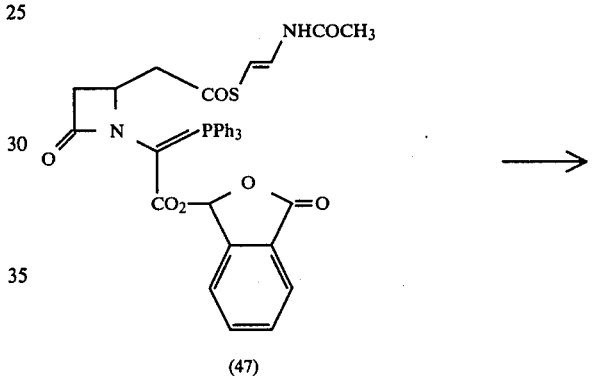

(47)

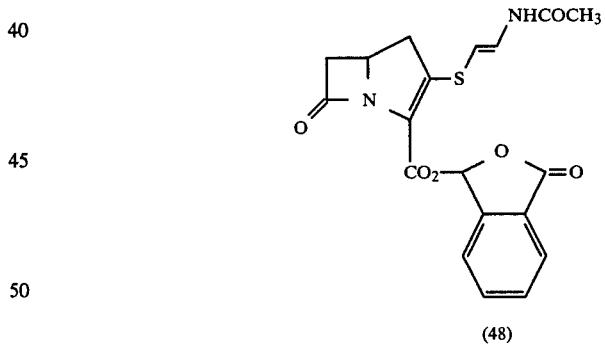

(48)

The phosphorane (47) (0.3 g) was dissolved in dry toluene (500 ml) and refluxed under argon with removal of water (Dean-Stark) for forty-eight hours. The solvent was evaporated and the residue chromatographed on Merck Keiselgel 60 (<230 mesh) using CHCL$_3$/EtOH as eluant. The product, which ran as the more polar component, was collected contaminated with starting phosphorane. Rechromatography gave separation of the starting phosphorane from the product (48) (0.003 g) $\lambda_{max}$ (EtOH) 331 nm $\nu_{max}$ 3440, 3325, 1785, 1700, 1625, 1270, 975 cm$^{-1}$.

We claim:
1. A compound of the formula:

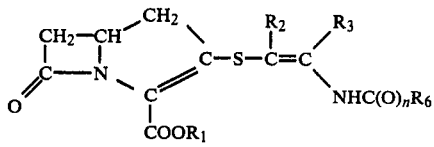

wherein
R₁ is hydrogen; a pharmaceutically acceptable cation; lower alkyl; lower alkyl substituted with lower alkoxy; benzyl; benzyl substituted with lower alkoxy, nitro or chloro; acetoxymethyl; pivaloyloxymethyl; α-ethoxycarbonyloxyethyl; or phthalidyl;
R₂ is hydrogen or lower alkyl;
R₃ is hydrogen or lower alkyl;
R₆ is phenyl or phenyl substituted with one or two members selected from the group consisting of fluoro, chloro, lower alkyl or lower alkoxy; and
n is 1 or 2.

2. A compound according to claim 1 wherein R₁ is hydrogen or a pharmaceutically acceptable cation and R₂ and R₃ are each hydrogen.

3. A compound according to claim 1 wherein R₁ is lower alkyl; lower alkyl substituted with lower alkoxy; benzyl, benzyl substituted with lower alkoxy, nitro or chloro; acetoxymethyl; pivaloyloxymethyl; α-ethoxycarbonyloxyethyl; or phthalidyl; and R₂ and R₃ are each hydrogen.

4. A compound according to claim 1 of the formula (III) or (IV):

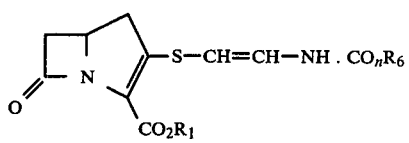

(III)

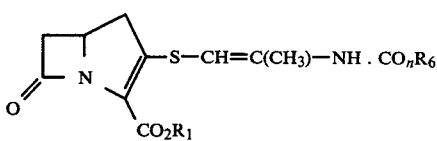

(IV)

wherein R₁ is a group such that CO₂R₁ is a carboxylic acid group or a salt thereof or is a group of the formula CO₂R₁¹ wherein R₁¹ is a group such that CO₂R₁¹ is an ester group, n is 1 or 2 and R₆ is lower alkyl.

5. a compound according to claim 2 wherein R₁ is a sodium, potassium, calcium or magnesium cation.

6. A compound according to claim 1 wherein R₁ is phthalidyl and R₂ and R₃ are each hydrogen.

7. A compound according to claim 1 wherein R₁ is p-nitrobenzyl and R₂ and R₃ are each hydrogen.

8. 3-(Z-2-Acetamidoethenylthio)-7-oxo-1-azabicyclo (3,2,0) hept-2-ene-2-carboxylic acid or a pharmaceutically acceptable salt or in-vivo hydrolsable ester thereof or 3-(E-2-acetamidoethenylthio)-7-oxo-1-azabicyclo (3,2,0) hept-2-ene-2-carboxylic acid or a pharmaceutically acceptable salt or in-vivo hydrolysable ester thereof.

9. A compound according to claim 1 in the form of the E isomer.

10. A compound according to claim 1 in the form of the Z isomer.

11. A compound according to claim 1 which is a mixture of the E and Z isomers.

12. A compound according to claim 1 having the S configuration aboutu C-5.

13. A compound according to claim 1 having the R configuration about C-5.

14. A compound according to claim 1 wherein R₂ is hydrogen or methyl, R₃ is hydrogen and R₆ is lower alkyl.

15. A compound according to claim 14 having the Z configuration.

16. The compound according to claim 15 which is 3-(Z-2-acetamidoethenylthio)-7-oxo-1-azabicyclo[3.2.0-]hept-2-ene-2-carboxylic acid.

17. A compound according to claim 14 having the E configuration.

18. The compound according to claim 17 which is 3-(E-2-acetamidoethenylthio)-7-oxo-1-azabicyclo[3.2.0-]hept-2-ene-2-carboxylic acid.

19. A pharmaceutical composition useful in the treatment of bacterial infections in humans and animals which comprises an antibacterially effective amount of at least one compound of the formula:

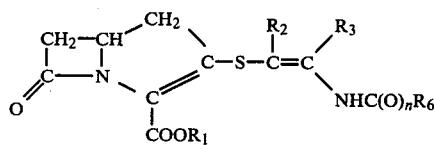

wherein
R₁ is hydrogen; a pharmaceutically acceptable cation; lower alkyl; lower alkyl substituted with lower alkoxy; benzyl; benzyl substituted with lower alkoxy, nitro or chloro; acetoxymethyl; pivaloyloxymethyl; α-ethoxycarbonyloxyethyl; or phthalidyl;
R₂ is hydrogen or lower alkyl;
R₃ is hydrogen or lower alkyl;
R₆ is phenyl or phenyl substituted with one or two members selected from the group consisting of fluoro, chloro, lower alkyl or lower alkoxy; and
n is 1 and 2, in combination with a pharmaceutically acceptable carrier.

20. A pharmaceutical composition according to claim 19 wherein R₁ is hydrogen or a pharmaceutically acceptable cation and R₂ and R₃ are each hydrogen.

21. A pharmaceutical composition according to claim 19 wherein R₁ is lower alkyl; lower alkyl substituted with lower alkoxy; benzyl; benzyl substituted with lower alkoxy, nitro or chloro; acetoxymethyl; pivaloyloxymethyl; α-ethoxycarbonyloxyethyl; or phthalidyl; and R₂ and R₃ are each hydrogen.

22. A pharmaceutical composition according to claim 19 wherein R₂ is hydrogen or methyl, R₃ is hydrogen and R₆ is lower alkyl.

23. A pharmaceutical composition according to claim 19 wherein R₁ is a sodium, potassium, calcium or magnesium cation.

24. A pharmaceutical composition according to claim 19 wherein R₁ is phthalidyl and R₂ and R₃ are each hydrogen.

25. A pharmaceutical composition according to claim 19 wherein R₁ is p-nitrobenzyl and R₂ and R₃ are each hydrogen.

26. A pharmaceutical composition according to claim 19 wherein said compound is in the form of the E isomer.

27. A pharmaceutical composition according to claim 19 wherein said compound is in the form of the Z isomer.

28. A pharmaceutical composition according to claim 19 wherein said compound is a mixture of the E and Z isomers.

29. a pharmaceutical composition according to claim 19 wherein said compound has the S configuration about C-5.

30. a pharmaceutical composition according to claim 19 wherein said compound has the R configuration about C-5.

31. a pharmaceutical composition according to claim 19 wherein said compound is 3-(Z-2-acetamidoethenylthio)-7-oxo-1-azabicyclo[3.2.0]hept-2-ene-2-carboxylic acid.

32. A pharmaceutical composition according to claim 19 wherein said compound is 3-(E-2-acetamidoethenylthio)-7-oxo-1-azabicyclo[3.2.0]hept-2-ene-2-carboxylic acid.

33. A method of treating bacterial infections in humans and animals which comprises administering to a human or animal in need thereof, an antibacterially effective amount of a compound of the formula:

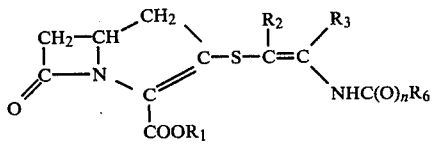

wherein
R$_1$ is hydrogen; a pharmaceutically acceptable cation; lower alkyl; lower alkyl substituted with lower alkoxy; benzyl; benzyl substituted with lower alkoxy, nitro or chloro; acetoxymethyl; pivaloyloxymethyl; α-ethoxycarbonyloxyethyl; or phthalidyl;
R$_2$ is hydrogen or lower alkyl;
R$_3$ is hydrogen or lower alkyl;
R$_6$ is phenyl or phenyl substituted with one or two members selected from the group consisting of fluoro, chloro, lower alkyl or lower alkoxy; and
n is 1 or 2.

34. The method according to claim 33 wherein R$_1$ is hydrogen or a pharmaceutically acceptable cation and R$_2$ and R$_3$ are each hydrogen.

35. The method according to claim 33 wherein R$_1$ is lower alkyl; lower alkyl substituted with lower alkoxy; benzyl; benzyl substituted with lower alkoxy, nitro or chloro, acetoxymethyl; pivaloyloxymethyl; α-ethoxycarbonyloxyethyl; or phthalidyl; and R$_2$ and R$_3$ are each hydrogen.

36. The method according to claim 33 wherein R$_2$ is hydrogen or methyl, R$_3$ is hydrogen and R$_6$ is lower alkyl.

37. The method according to claim 33 wherein R$_1$ is a sodium, potassium, calcium or magnesium cation.

38. The method according to claim 33 wherein R$_1$ is phthalidyl and R$_2$ and R$_3$ are each hydrogen.

39. The method according to claim 33 wherin R$_1$ is p-nitrobenzyl and R$_2$ and R$_3$ are each hydrogen.

40. The method according to claim 33 wherein said compound is in the form of the E isomer.

41. The method according to claim 33 wherein said compound is in the form of the Z isomer.

42. The method according to claim 33 wherein said compound is a mixture of the E and Z isomers.

43. The method according to claim 33 wherein said compound has the S configuration about C-5.

44. The method according to claim 33 wherein said compound has the R configuration about C-5.

45. The method according to claim 33 wherein said compound is 3-(Z-2-acetamidoethenylthio)-7-oxo-1-azabicyclo[3.2.0]-hept-2-end-2-carboxylic acid.

46. The method according to claim 33 wherein said compound is 3-(E-2-acetamidoethenylthio)-7-oxo-1-azabicyclo[3.2.0]-hept-2-ene-2-carboxylic acid.

* * * * *

UNITED STATES PATENT AND TRADEMARK OFFICE
CERTIFICATE OF CORRECTION

PATENT NO. : 4,255,441
DATED : March 10, 1981
INVENTOR(S) : ROGER J. PONSFORD ET AL.

It is certified that error appears in the above-identified patent and that said Letters Patent are hereby corrected as shown below:

In the foreign application priority data, please add:

January 10, 1979  United Kingdom  00935/79

Signed and Sealed this

Second Day of February 1982

[SEAL]

Attest:

GERALD J. MOSSINGHOFF

Attesting Officer   Commissioner of Patents and Trademarks